United States Patent
Bosse

(10) Patent No.: US 9,427,407 B2
(45) Date of Patent: *Aug. 30, 2016

(54) PHARMACEUTICAL COMPOSITIONS

(71) Applicant: LOCL PHARMA, INC., Las Vegas, NV (US)

(72) Inventor: Paul Bosse, Jupiter, FL (US)

(73) Assignee: LOCL PHARMA, INC., Las Vegas, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/748,621

(22) Filed: Jun. 24, 2015

(65) Prior Publication Data

US 2015/0328213 A1 Nov. 19, 2015

Related U.S. Application Data

(63) Continuation of application No. 14/099,432, filed on Dec. 6, 2013, which is a continuation of application No. 12/444,521, filed as application No. PCT/US2007/080831 on Oct. 9, 2007, now Pat. No. 8,653,066.

(60) Provisional application No. 60/948,375, filed on Jul. 6, 2007, provisional application No. 60/921,563, filed on Apr. 3, 2007, provisional application No. 60/850,451, filed on Oct. 9, 2006.

(51) Int. Cl.
| | |
|---|---|
| *A61K 31/485* | (2006.01) |
| *A61K 31/5415* | (2006.01) |
| *A61K 9/24* | (2006.01) |
| *A61K 9/20* | (2006.01) |
| *A61K 45/06* | (2006.01) |
| *A61K 31/167* | (2006.01) |

(52) U.S. Cl.
CPC ............... *A61K 9/209* (2013.01); *A61K 9/20* (2013.01); *A61K 9/2086* (2013.01); *A61K 31/167* (2013.01); *A61K 31/485* (2013.01); *A61K 31/5415* (2013.01); *A61K 45/06* (2013.01)

(58) Field of Classification Search
CPC .................. A61K 31/485; A61K 31/5415
See application file for complete search history.

(56) References Cited

U.S. PATENT DOCUMENTS

| | | | |
|---|---|---|---|
| 3,048,526 A | 8/1962 | Boswell | |
| 3,108,046 A | 10/1963 | Harbit | |
| 3,536,809 A | 10/1970 | Applezweig | |
| 3,598,123 A | 8/1971 | Zaffaroni | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 4,113,866 A | 9/1978 | Lednicer | |
| 4,265,875 A | 5/1981 | Byrne et al. | |
| 4,478,822 A | 10/1984 | Haslam et al. | |
| 4,532,126 A | 7/1985 | Ebert et al. | |
| 4,588,580 A | 5/1986 | Gale et al. | |
| 4,624,665 A | 11/1986 | Nuwayser | |
| 4,625,494 A | 12/1986 | Iwatschenko et al. | |
| 4,626,539 A | 12/1986 | Aungst et al. | |
| 4,671,953 A | 6/1987 | Stanley et al. | |
| 4,685,911 A | 8/1987 | Konno et al. | |
| 4,717,713 A | 1/1988 | Zatz et al. | |
| 4,786,505 A | 11/1988 | Lovgren et al. | |
| 4,788,055 A | 11/1988 | Fischer et al. | |
| 4,800,083 A | 1/1989 | Hom et al. | |
| 4,820,522 A | 4/1989 | Radebaugh et al. | |
| 4,834,978 A | 5/1989 | Nuwayser | |
| 4,853,211 A | 8/1989 | Kurobe et al. | |
| 4,871,353 A | 10/1989 | Thomsen | |
| 4,904,479 A | 2/1990 | Illum | |
| 4,906,463 A | 3/1990 | Cleary et al. | |
| 4,919,939 A | 4/1990 | Baker | |
| 4,925,444 A | 5/1990 | Orkin et al. | |
| 4,935,243 A | 6/1990 | Borkan et al. | |
| 4,950,484 A | 8/1990 | Othoff et al. | |
| 5,013,726 A | 5/1991 | Ivy et al. | |
| 5,055,461 A | 10/1991 | Kelleher et al. | |
| 5,059,595 A | 10/1991 | Le Grazie | |
| 5,073,543 A | 12/1991 | Marshall et al. | |
| 5,120,548 A | 6/1992 | Mcclelland et al. | |
| 5,266,331 A | 11/1993 | Oshlack et al. | |
| 5,298,520 A | 3/1994 | Baker et al. | |
| 5,354,556 A | 10/1994 | Sparks et al. | |
| 5,373,022 A | 12/1994 | Fawzi et al. | |
| 5,376,672 A | 12/1994 | Pilgrim | |
| 5,393,773 A | 2/1995 | Craig et al. | |
| 5,425,950 A | 6/1995 | Dandiker et al. | |
| 5,445,829 A | 8/1995 | Paradissis et al. | |
| 5,464,864 A | 11/1995 | King et al. | |
| 5,468,504 A | 11/1995 | Schaeffer et al. | |
| 5,478,577 A | 12/1995 | Sackler et al. | |
| 5,484,406 A | 1/1996 | Wong et al. | |
| 5,508,042 A | 4/1996 | Oshlack et al. | |
| 5,536,249 A | 7/1996 | Castellano et al. | |
| 5,549,912 A | 8/1996 | Oshlack et al. | |

(Continued)

FOREIGN PATENT DOCUMENTS

| | | |
|---|---|---|
| CA | 2262267 A1 | 8/1999 |
| DE | 102005013726 A1 | 9/2006 |

(Continued)

OTHER PUBLICATIONS

U.S. Pat. No. 8,975,271, Mar. 10, 2015, Oshlack et al. (withdrawn).

(Continued)

*Primary Examiner* — Samira Jean-Louis

(74) *Attorney, Agent, or Firm* — Wilson Sonsini Goodrich & Rosati

(57) ABSTRACT

Pharmaceutical compositions are provided which comprise effective amounts of analgesic to treat a subject, including to reduce or eliminate an adverse effect associated with the analgesic.

35 Claims, 4 Drawing Sheets

(56) References Cited

U.S. PATENT DOCUMENTS

| | | |
|---|---|---|
| 5,554,639 A | 9/1996 | Craig et al. |
| 5,585,115 A | 12/1996 | Sherwood et al. |
| 5,591,767 A | 1/1997 | Mohr et al. |
| 5,602,162 A | 2/1997 | Baker et al. |
| 5,610,184 A | 3/1997 | Shahinian, Jr. |
| 5,629,333 A | 5/1997 | Young |
| 5,635,204 A | 6/1997 | Gevirtz et al. |
| 5,637,611 A | 6/1997 | King et al. |
| 5,639,476 A | 6/1997 | Oshlack et al. |
| 5,656,295 A | 8/1997 | Oshlack et al. |
| 5,674,533 A | 10/1997 | Santus et al. |
| 5,705,506 A | 1/1998 | Merlet et al. |
| 5,705,520 A | 1/1998 | Craig et al. |
| 5,712,302 A | 1/1998 | Young |
| 5,733,556 A | 3/1998 | Schrier et al. |
| 5,738,874 A | 4/1998 | Conte et al. |
| 5,741,510 A | 4/1998 | Rolf et al. |
| 5,827,852 A | 10/1998 | Russell et al. |
| 5,827,871 A | 10/1998 | King et al. |
| 5,837,284 A | 11/1998 | Mehta et al. |
| 5,840,731 A | 11/1998 | Mayer et al. |
| 5,854,270 A | 12/1998 | Gambhir |
| 5,863,559 A | 1/1999 | Phillips et al. |
| 5,863,922 A | 1/1999 | Mayer et al. |
| 5,866,161 A | 2/1999 | Childers et al. |
| 5,871,776 A | 2/1999 | Mehta |
| 5,891,885 A | 4/1999 | Caruso |
| 5,895,663 A | 4/1999 | Irwin et al. |
| 5,902,632 A | 5/1999 | Mehta |
| 5,919,479 A | 7/1999 | Zhang et al. |
| 5,929,059 A | 7/1999 | Sanger et al. |
| 5,954,700 A | 9/1999 | Kovelman |
| 5,962,494 A | 10/1999 | Young |
| 5,968,551 A | 10/1999 | Oshlack et al. |
| 6,020,001 A | 2/2000 | Phillips et al. |
| 6,063,802 A | 5/2000 | Winterborn |
| 6,146,361 A | 11/2000 | Dibiasi et al. |
| 6,160,020 A | 12/2000 | Ohannesian et al. |
| 6,228,398 B1 | 5/2001 | Devane et al. |
| 6,228,863 B1 | 5/2001 | Palermo et al. |
| 6,255,502 B1 | 7/2001 | Penkler et al. |
| 6,258,380 B1 | 7/2001 | Overholt |
| 6,261,595 B1 | 7/2001 | Stanley et al. |
| 6,287,600 B1 | 9/2001 | Ouali et al. |
| 6,303,142 B1 | 10/2001 | Zhang et al. |
| 6,335,033 B2 | 1/2002 | Oshlack et al. |
| 6,341,387 B1 | 1/2002 | Zars |
| 6,348,216 B1 | 2/2002 | Kushla et al. |
| 6,368,627 B1 | 4/2002 | Phillips et al. |
| 6,372,254 B1 | 4/2002 | Ting et al. |
| 6,376,550 B1 | 4/2002 | Raber et al. |
| 6,465,006 B1 | 10/2002 | Zhang et al. |
| 6,469,227 B1 | 10/2002 | Cooke et al. |
| 6,475,494 B2 | 11/2002 | Kaiko et al. |
| 6,482,435 B1 | 11/2002 | Stratton et al. |
| 6,491,945 B1 | 12/2002 | Childers et al. |
| 6,572,871 B1 | 6/2003 | Church et al. |
| 6,572,885 B2 | 6/2003 | Oshlack et al. |
| 6,599,531 B2 | 7/2003 | Kushla et al. |
| 6,613,350 B1 | 9/2003 | Zhang et al. |
| 6,649,183 B2 | 11/2003 | Rubin et al. |
| 6,699,502 B1 | 3/2004 | Fanara et al. |
| 6,730,325 B2 | 5/2004 | Devane et al. |
| 6,733,783 B2 | 5/2004 | Oshlack et al. |
| 6,756,053 B2 | 6/2004 | Zhang et al. |
| 6,756,056 B2 | 6/2004 | Rubin |
| 6,780,426 B2 | 8/2004 | Zhang et al. |
| 6,827,946 B2 | 12/2004 | Hirsh |
| 6,855,332 B2 | 2/2005 | Gizurarson et al. |
| 6,902,742 B2 | 6/2005 | Devane et al. |
| 6,913,768 B2 | 7/2005 | Couch et al. |
| 6,923,988 B2 | 8/2005 | Patel et al. |
| 6,976,647 B2 | 12/2005 | Reed et al. |
| 7,029,698 B2 | 4/2006 | Waranis et al. |
| RE39,221 E | 8/2006 | Raffa et al. |
| 7,094,228 B2 | 8/2006 | Zhang et al. |
| 7,172,767 B2 | 2/2007 | Kaiko et al. |
| 7,201,920 B2 | 4/2007 | Kumar et al. |
| 7,214,385 B2 | 5/2007 | Gruber |
| 7,214,711 B2 | 5/2007 | Hochman |
| 7,332,183 B2 | 2/2008 | Plachetka et al. |
| 7,342,028 B2 | 3/2008 | Hagan et al. |
| 7,514,100 B2 | 4/2009 | Oshlack et al. |
| 7,585,493 B2 | 9/2009 | Hale et al. |
| 7,585,520 B2 | 9/2009 | Hirsh et al. |
| 7,666,337 B2 | 2/2010 | Yang et al. |
| 7,744,916 B2 | 6/2010 | Pauletti et al. |
| 7,794,750 B2 | 9/2010 | Naringrekar et al. |
| 7,863,296 B2 | 1/2011 | Weiner et al. |
| 7,943,174 B2 | 5/2011 | Oshlack et al. |
| 8,022,095 B2 | 9/2011 | Plachetka |
| 8,124,126 B2 | 2/2012 | Bosse et al. |
| 8,236,328 B2 | 8/2012 | Babcock et al. |
| 8,263,126 B2 | 9/2012 | Oury et al. |
| 8,268,791 B2 | 9/2012 | Maggio |
| 8,597,681 B2 | 12/2013 | Park et al. |
| 8,632,805 B2 | 1/2014 | Naringrekar et al. |
| 8,637,503 B2 | 1/2014 | Boland et al. |
| 8,653,066 B2 | 2/2014 | Bosse |
| 8,703,196 B2 | 4/2014 | Babcock et al. |
| 8,728,522 B2 | 5/2014 | Bosse et al. |
| 8,822,489 B2 | 9/2014 | Kumar et al. |
| 8,920,837 B2 | 12/2014 | Pilgaonkar et al. |
| 9,034,377 B2 | 5/2015 | Wright et al. |
| 9,044,435 B2 | 6/2015 | Wright et al. |
| 9,226,901 B2 | 1/2016 | Bosse et al. |
| 2003/0008892 A1 | 1/2003 | Coe et al. |
| 2003/0068375 A1 | 4/2003 | Wright et al. |
| 2003/0092724 A1 | 5/2003 | Kao et al. |
| 2003/0133982 A1 | 7/2003 | Heimlich et al. |
| 2003/0181462 A1 | 9/2003 | Doods et al. |
| 2003/0225002 A1 | 12/2003 | Livingstone |
| 2004/0019080 A1 | 1/2004 | Sheftell et al. |
| 2004/0043071 A1 | 3/2004 | Pauletti et al. |
| 2004/0047907 A1 | 3/2004 | Oshlack et al. |
| 2004/0136913 A1 | 7/2004 | Dugger et al. |
| 2004/0136914 A1 | 7/2004 | Dugger et al. |
| 2004/0152713 A1 | 8/2004 | Petrie |
| 2004/0156859 A1 | 8/2004 | Ezrin et al. |
| 2004/0156903 A1 | 8/2004 | Abrams et al. |
| 2004/0167200 A1 | 8/2004 | Coe et al. |
| 2004/0170680 A1 | 9/2004 | Oshlack et al. |
| 2004/0185096 A1 | 9/2004 | Oshlack et al. |
| 2004/0195413 A1 | 10/2004 | Reed et al. |
| 2004/0213828 A1 | 10/2004 | Smith |
| 2004/0241159 A1 | 12/2004 | De Cellery et al. |
| 2004/0248956 A1 | 12/2004 | Hagmann et al. |
| 2004/0266807 A1 | 12/2004 | Oshlack et al. |
| 2005/0074493 A1 | 4/2005 | Mehta et al. |
| 2005/0080012 A1 | 4/2005 | Mickle et al. |
| 2005/0084530 A1 | 4/2005 | Rao et al. |
| 2005/0106249 A1 | 5/2005 | Hwang et al. |
| 2005/0147710 A1 | 7/2005 | Teckoe et al. |
| 2005/0158382 A1 | 7/2005 | Cruz et al. |
| 2005/0163856 A1 | 7/2005 | Maloney et al. |
| 2005/0232986 A1 | 10/2005 | Brown et al. |
| 2005/0232987 A1 | 10/2005 | Srinivasan et al. |
| 2005/0232993 A1 | 10/2005 | Brown et al. |
| 2005/0266032 A1 | 12/2005 | Srinivasan et al. |
| 2005/0272810 A1 | 12/2005 | Davis et al. |
| 2005/0281875 A1 | 12/2005 | Srinivasan et al. |
| 2005/0282879 A1 | 12/2005 | Salehani |
| 2006/0009512 A1 | 1/2006 | Curwen et al. |
| 2006/0029664 A1 | 2/2006 | Srinivasan et al. |
| 2006/0057205 A1 | 3/2006 | Srinivasan et al. |
| 2006/0073189 A1 | 4/2006 | Pinney et al. |
| 2006/0110327 A1 | 5/2006 | Emigh et al. |
| 2006/0127479 A1 | 6/2006 | Kumaraperumal et al. |
| 2006/0134207 A1 | 6/2006 | Srinivasan et al. |
| 2006/0142273 A1 | 6/2006 | Rudolf et al. |
| 2006/0165604 A1 | 7/2006 | Dugger, III et al. |
| 2006/0177380 A1 | 8/2006 | Emigh et al. |
| 2006/0183693 A1 | 8/2006 | Doods et al. |
| 2006/0198790 A1 | 9/2006 | Dugger, III et al. |

(56) References Cited

U.S. PATENT DOCUMENTS

| | | |
|---|---|---|
| 2006/0204578 A1 | 9/2006 | Vergez et al. |
| 2006/0240105 A1 | 10/2006 | Devane et al. |
| 2007/0003622 A1 | 1/2007 | Srinivasan et al. |
| 2007/0059254 A1 | 3/2007 | Singh |
| 2007/0060500 A1 | 3/2007 | Mickle et al. |
| 2007/0099849 A1 | 5/2007 | Livingstone |
| 2007/0148097 A1 | 6/2007 | Finn et al. |
| 2007/0166336 A1 | 7/2007 | Delmarre et al. |
| 2007/0191462 A1 | 8/2007 | Hettiarachchi et al. |
| 2007/0231268 A1 | 10/2007 | Emigh et al. |
| 2007/0286875 A1 | 12/2007 | Dagar et al. |
| 2008/0044482 A1 | 2/2008 | Oshlack et al. |
| 2008/0057122 A1 | 3/2008 | Toney-Parker et al. |
| 2008/0074208 A1 | 3/2008 | Lee |
| 2008/0075781 A1 | 3/2008 | Oshlack et al. |
| 2008/0103134 A1 | 5/2008 | Rudolf et al. |
| 2008/0131517 A1 | 6/2008 | Fawzy et al. |
| 2008/0181941 A1 | 7/2008 | Oshlack et al. |
| 2008/0213343 A1 | 9/2008 | Obermeier et al. |
| 2008/0292699 A1 | 11/2008 | Brown et al. |
| 2009/0004281 A1 | 1/2009 | Nghiem et al. |
| 2009/0068269 A1 | 3/2009 | Oshlack et al. |
| 2009/0118170 A1 | 5/2009 | Dugger, III |
| 2009/0124554 A1 | 5/2009 | Dugger, III |
| 2009/0156581 A1 | 6/2009 | Dillon et al. |
| 2009/0162297 A1 | 6/2009 | Dugger, III et al. |
| 2009/0162298 A1 | 6/2009 | Dugger, III et al. |
| 2009/0163451 A1 | 6/2009 | Porreca et al. |
| 2009/0175939 A1 | 7/2009 | Bosse et al. |
| 2009/0232898 A1 | 9/2009 | Pettersson et al. |
| 2009/0311335 A1 | 12/2009 | Jenkins et al. |
| 2010/0008995 A1 | 1/2010 | Duncalf et al. |
| 2010/0112050 A1 | 5/2010 | Ryoo et al. |
| 2010/0143469 A1 | 6/2010 | Bosse |
| 2010/0144754 A1 | 6/2010 | Peltz et al. |
| 2010/0159007 A1 | 6/2010 | Staniforth |
| 2010/0160378 A1 | 6/2010 | Maggio |
| 2010/0196471 A1 | 8/2010 | Jain et al. |
| 2011/0066100 A1 | 3/2011 | Sebree et al. |
| 2011/0077272 A1 | 3/2011 | Main |
| 2011/0105441 A1 | 5/2011 | Zhang et al. |
| 2011/0118189 A1 | 5/2011 | Farr et al. |
| 2011/0262539 A1 | 10/2011 | Bosse et al. |
| 2012/0201888 A1 | 8/2012 | Bosse et al. |
| 2012/0202866 A1 | 8/2012 | Dugger, III et al. |
| 2014/0030322 A1 | 1/2014 | Bosse et al. |
| 2014/0073678 A1 | 3/2014 | Dadey et al. |
| 2014/0112981 A1 | 4/2014 | Oshlack et al. |
| 2014/0134248 A1 | 5/2014 | Bosse |
| 2014/0221416 A1 | 8/2014 | Guido et al. |
| 2014/0271896 A1 | 9/2014 | Abu et al. |
| 2014/0308349 A1 | 10/2014 | Bosse et al. |
| 2014/0323512 A1 | 10/2014 | Mckenna |
| 2014/0357658 A1 | 12/2014 | Kaiko et al. |
| 2015/0030677 A1 | 1/2015 | Adjei et al. |
| 2015/0290211 A1 | 10/2015 | Bosse et al. |
| 2015/0297525 A1 | 10/2015 | Bosse et al. |
| 2015/0306040 A1 | 10/2015 | Bosse et al. |
| 2015/0320685 A1 | 11/2015 | Bosse et al. |
| 2015/0328161 A1 | 11/2015 | Bosse |
| 2015/0328209 A1 | 11/2015 | Bosse |
| 2015/0328210 A1 | 11/2015 | Bosse |
| 2015/0328211 A1 | 11/2015 | Bosse |
| 2015/0328212 A1 | 11/2015 | Bosse |
| 2016/0051474 A1 | 2/2016 | Bosse et al. |

FOREIGN PATENT DOCUMENTS

| | | | |
|---|---|---|---|
| FR | 2787713 A1 | 6/2000 | |
| WO | WO 97/18801 A1 | 5/1997 | |
| WO | WO 99/42095 A1 | 8/1999 | |
| WO | WO 02/080953 A2 | 10/2002 | |
| WO | WO 02/080953 A3 | 12/2002 | |
| WO | WO 2006/022996 A2 | 3/2006 | |
| WO | WO 2006/103418 A1 | 10/2006 | |
| WO | WO 2006/022996 A3 | 12/2006 | |
| WO | WO 2007/035573 A2 | 3/2007 | |
| WO | WO 2007/035573 A3 | 6/2007 | |
| WO | WO 2007/130507 A2 | 11/2007 | |
| WO | WO 2008/027350 A2 | 3/2008 | |
| WO | WO 2008/027350 A3 | 5/2008 | |
| WO | WO 2008/070268 A2 | 6/2008 | |
| WO | WO 2008/074419 A1 | 6/2008 | |
| WO | WO 2008/070268 A3 | 11/2008 | |
| WO | WO 2009/089494 A2 | 7/2009 | |
| WO | WO 2009/089494 A3 | 1/2010 | |
| WO | WO 2010/062688 A2 | 6/2010 | |
| WO | WO 2011/006012 A1 | 1/2011 | |
| WO | WO 2010/062688 A3 | 5/2012 | |
| WO | WO 2014/043346 A2 | 3/2014 | |

OTHER PUBLICATIONS

Office action dated Aug. 14, 2015 for U.S. Appl. No. 14/789,883.
Office action dated Aug. 14, 2015 for U.S. Appl. No. 14/789,886.
Office action dated Sep. 8, 2015 for U.S. Appl. No. 14/748,605.
Office action dated Sep. 8, 2015 for U.S. Appl. No. 14/748,609.
Office action dated Sep. 10, 2015 for U.S. Appl. No. 14/748,617.
Office action dated Sep. 17, 2015 for U.S. Appl. No. 14/244,455.
Office action dated Sep. 17, 2015 for U.S. Appl. No. 14/748,614.
Office action dated Sep. 18, 2015 for U.S. Appl. No. 14/789,888.
U.S. Appl. No. 60/948,375, filed Jul. 6, 2007, Bosse.
U.S. Appl. No. 61/020,139, filed Jan. 9, 2008, Bosse et al.
U.S. Appl. No. 61/043,037, filed Apr. 7, 2008, Bosse et al.
U.S. Appl. No. 61/060,758, filed Jun. 11, 2008, Bosse et al.
U.S. Appl. No. 61/223,999, filed Jul. 8, 2009, Bosse et al.
U.S. Appl. No. 61/224,424, filed Jul. 9, 2009, Bosse et al.
U.S. Appl. No. 14/683,886, filed Apr. 10, 2015, Bosse et al.
U.S. Appl. No. 14/748,605, filed Jun. 24, 2015, Bosse.
U.S. Appl. No. 14/748,609, filed Jun. 24, 2015, Bosse.
U.S. Appl. No. 14/748,613, filed Jun. 24, 2015, Bosse.
U.S. Appl. No. 14/748,614, filed Jun. 24, 2015, Bosse.
U.S. Appl. No. 14/748,617, filed Jun. 24, 2015, Bosse.
U.S. Appl. No. 14/789,883, filed Jul. 1, 2015, Bosse et al.
U.S. Appl. No. 14/789,886, filed Jul. 1, 2015, Bosse et al.
U.S. Appl. No. 14/789,888, filed Jul. 1, 2015, Bosse et al.
Alexander, et al. Comparison of ondansetron and droperidol in reducing postoperative nausea and vomiting associated with patient-controlled analgesia. Anaesthesia. Dec. 1995;50(12):1086-8.
Apfel, et al. A factorial trial of six interventions for the prevention of postoperative nausea and vomiting. N Engl J Med. Jun. 10, 2004;350(24):2441-51.
Braude, et al. Ondansetron versus promethazine to treat acute undifferentiated nausea in the emergency department: a randomized, double-blind, noninferiority trial. Acad Emerg Med. Mar. 2008;15(3):209-15. doi: 10.1111/j.1553-2712.2008.00060.x.
Charleston Laboratories' Investigational New Drug Application, pp. 93-94, filed with the U.S. Food and Drug Administration on Sep. 5, 2008. Charleston Laboratories is the assignee of the present application.
Chia, et al. The effect of promethazine on postoperative pain: a comparison of preoperative, postoperative, and placebo administration in patients following total abdominal hysterectomy. Acta Anaesthesiol Scand. May 2004;48(5):625-30.
Davis. Hydrocodone. Opioids for cancer pain. Oxford UK: Oxford University Press. 2005. pp. 59-68. ISBN 0-19-852943-0.
European search report dated Nov. 19, 2014 for EP Application No. 14177981.9.
Foster, et al. Complicated pain management in a CYP450 2D6 poor metabolizer. Pain Pract. Dec. 2007;7(4):352-6.
Hardy, et al. A double-blind, randomised, parallel group, multinational, multicentre study comparing a single dose of ondansetron 24 mg p.o. with placebo and metoclopramide 10 mg t.d.s. p.o. in the treatment of opioid-induced nausea and emesis in cancer patients. Support Care Cancer. Apr. 2002;10(3):231-6.
International preliminary report on patentability dated Jul. 22, 2010 for PCT Application No. PCT/US09/30662.

(56) References Cited

OTHER PUBLICATIONS

International search report and written opinion dated Jun. 17, 2015 for PCT Application No. US2015/025481.
International search report dated May 22, 2009 for Application No. US2009/30662.
International search report dated Sep. 1, 2010 for PCT Application No. PCT/US2010/41433.
International search report dated Sep. 23, 2008 for Application No. PCT/US2007/80831.
Kovac, A. Prophylaxis of postoperative nausea and vomiting: controversies in the use of serotonin 5-hydroxytryptamine subtype 3 receptor antagonists. J Clin Anesth. Jun. 2006;18(4):304-18.
Mayo Clinic Website. Cough and Cold Combination (Oral Route). Available at www.mayoclinic.com/health/drug-infomation/DR602361. Accessed Oct. 2, 2007.
Moser, et al. No more than necessary: Safety and efficacy of low-dose promethazine. Annals of Pharmacotherapy. 2006; 40:45-48.
Notice of allowance dated Jan. 28, 2014 for U.S. Appl. No. 12/967,423.
Notice of allowance dated Oct. 7, 2013 for U.S. Appl. No. 12/444,521.
Notice of allowance dated Oct. 11, 2011 for U.S. Appl. No. 12/351,704.
Office action dated Feb. 7, 2013 for U.S. Appl. No. 12/444,521.
Office action dated Feb. 29, 2012 for U.S. Appl. No. 12/967,423.
Office action dated Mar. 27, 2015 for U.S. Appl. No. 14/036,946.
Office action dated Jun. 29, 2012 for U.S. Appl. No. 12/444,521.
Office action dated Jul. 17, 2014 for U.S. Appl. No. 13/347,552.
Office action dated Sep. 6, 2012 for U.S. Appl. No. 12/967,423.
Office action dated Sep. 20, 2010 for U.S. Appl. No. 12/351,704.
Office action dated Oct. 8, 2014 for U.S. Appl. No. 14/036,946.
Oldfield, et al. Oxycodone/Ibuprofen combination tablet: a review of its use in the management of acute pain. Drugs. 2005;65(16):2337-54.
Palangio, et al. Combination hydrocodone and ibuprofen versus combination oxycodone and acetaminophen in the treatment of moderate or severe acute low back pain. Clin Ther. Jan. 2002;24(1):87-99.
Paoloni, et al. Low incidence of nausea and vomiting with intravenous opiate analgesia in the ED. Am J Emerg Med. Nov. 2002;20(7):604-8.
Promethazine HCI and Hydrocodone Bitartrate Syrup. WraSer Pharmaceuticals, Madison, MS. Jan. 2007.
Prosolve Data Sheet [online] retrieved on Feb. 27, 2012 from: http://www.jrspharma.de/Pharma/wEnglisch/produktinfo/prosolv_smcc/prosolv_smcc_grades.shtml; 2 pages.
Ragg, et al. Comparison of the efficacy of paracetamol versus paracetamol, codeine and promethazine (Painstop) for premedication and analgesia for myringotomy in children. Anaesth Intensive Care. Feb. 1997;25(1):29-32.
Richmond, B. S. Pharmacy & Therapeutics Committees. Antiemetic Prophylaxis and Treatment of Postoperative and Opioid-Induced Nausea and Vomiting. Jul. 2007.
Schachtel, et al. Demonstration of the safety and efficacy of CL-108 for moderate-to-severe pain with reduction of opioid-induced nausea and vomiting. Abstract No. 420, Journal of Pain, Apr. 2014, vol. 15, No. 4, Supp. SUPPL. 1, p. S81, 33rd Annual Scientific Meeting of the American Pain Society, Apr. 30, 2014-May 3, 2014.
Shafer, et al. The Roche friabilator. J Am Pharm Assoc. Feb. 1956;45(2 Part 1):114-6.
Silverman, et al. Influence of promethazine on symptom-therapy scores for nausea during patient-controlled analgesia with morphine. Anesth Analg. May 1992;74(5):735-8.
Strenkoski-Nix, et al. Pharmacokinetics of promethazine hydrochloride after administration of rectal suppositories and oral syrup to healthy subjects. Am J Health Syst Pharm. Aug. 15, 2000;57(16):1499-505.
Suzuki Takahiro. Utilize codeine phosphate. Journal of Pain and Clinical Medicine (2006), vol. 6, No. 1, p. 77-82. (in Japanese with English translation).
Takeda, et al. Strong opioid analgesics in cancer pain management—starting timing of administration. Cancer patient and symptomatic therapy 2003, vol. 14, No. 2, pp. 24-28 (in Japanese with English translation by Machine).
Tarkkila, et al. Premedication with promethazine and transdermal scopolamine reduces the incidence of nausea and vomiting after intrathecal morphine. Acta Anaesthesiol Scand. Oct. 1995;39(7):983-6.
U.S. Pharmacopeia National Formulary Supplement. USP 23-NF 18, 9th dated Nov. 15, 1998, p. 4678.
Vinson, D.R. Treatment patterns of isolated benign headache in US emergency departments. Ann Emerg Med. Mar 2002;39(3):215-22. (Abstract).
Watcha, et al. Postoperative nausea and vomiting. Its etiology, treatment, and prevention. Anesthesiology. Jul. 1992;77(1):162-84.
Wikipedia. Acetaminophen. en.wikipedia.org/wiki/Acetaminophen. Last Accessed Aug. 22, 2012.
Wikipedia. Hydrocodone. en.wikipedia.org/wiki/Hydrocodone Last Accessed Aug. 22, 2012.
Yaghmour, et al. Multimodal Anesthesia and Analgesia Facilitates Ambulatory Discharge of Patients Undergoing Osseous Reconstructive Ankle Surgery (RAS). Anesthesiology 2003; 99: A19 URL:http://www.asaabstracts.com/strands/asaabstracts/abstract.htm;jsessionid=D8FB91F2211878C2D0D08A062AA48B1E?year=2003&index=1&absnum=1516.
U.S. Appl. No. 14/930,496, filed Nov. 2, 2015, Bosse et al.
Meert, et al. A preclinical comparison between different opioids: antinociceptive versus adverse effects. Pharmacol Biochem Behav. Feb. 2005;80(2):309-26. Epub Jan. 7, 2005.
Package Insert. DURAGESIC. Janssen Pharmaceutica Products. 2003.
Package Insert. OXYCONTIN. Purdue Pharma L.P. Sep. 7, 2007.
"Guidance for Industry: Statistical Approaches to Establishing Bioequivalence" U.S. Department of Health and Human Services Food and Drug Administration Center for Drug Evaluation and Research (CDER) Jan. 2001.
"Guidance for Industry: Bioavailability and Bioequivalence Studies for Orally Administered Drug Products—General Considerations" U.S. Department of Health and Human Services Food and Drug Administration Center for Drug Evaluation and Research (CDER) Mar. 2003.
Amdipharm Plc. Opioid-induced nausea and vomiting. Web Site by Nexus Internet Solutions Ltd. Apr. 2004.
Amo, et al. Subchronic and chronic effects of feeding of large amounts of acetaminophen in B6C3F1 mice. Jap J Hyg. 40:567-574, 1985.
Anderson. Paracetamol (Acetaminophen): mechanisms of action. Paediatr Anaesth. Oct. 2008;18(10):915-21. doi: 10.1111/j.1460-9592.2008.02764.x.
Anesthetic, Analgesic, Rheumatic Drugs Division, Pre-IND Meeting with Charleston Laboratories, Inc. Nov. 8, 2007, Silver Springs, MD.
Aparasu, et al. Opioid-induced emesis among hospitalized nonsurgical patients: effect on pain and quality of life. J Pain Symptom Manage. Oct. 1999;18(4):280-8.
Apfel, et al. A risk score to predict the probability of postoperative vomiting in adults. Acta Anaesthesiol Scand. May 1998;42(5):495-501.
Apfel, et al. A simplified risk score for predicting postoperative nausea and vomiting: conclusions from cross-validations between two centers. Anesthesiology. Sep. 1999;91(3):693-700.
Apfel, et al. The discriminating power of a risk score for postoperative vomiting in adults undergoing various types of surgery. Acta Anaesthesiol Scand. May 1998;42(5):502-9.
Apfelbaum, et al. Reliability and validity of the perioperative opioid-related symptom distress scale. Anesth Analg. Sep. 2004;99(3):699-709, table of contents.
Armstrong, et al. Pharmacokinetic drug interactions of morphine, codeine, and their derivatives: Theory and clinical reality, Part II. Psychosomatics. 44(6):515-20, 2003.

(56) References Cited

OTHER PUBLICATIONS

Aronson, et al. Aronson CE, Hanno ERS. Effect of promethazine on the isolated perfused rat heart. Gen Pharmacol. 10:389-395, 1979.
Atkinson, et al. Hierarchical construct validity of the treatment satisfaction questionnaire for medication (TSQM version II) among outpatient pharmacy consumers. Value Health. Nov.-Dec. 2005;8 Suppl 1:S9-S24.
Balster, et al. Guidelines and methodological reviews concerning drug abuse liability assessment. Drug Alcohol Depend. Jun. 5, 2003;70(3 Suppl):S13-40.
Barkin. Acetaminophen, aspirin, or Ibuprofen in combination analgesic products. Am J Ther. Nov.-Dec. 2001;8(6):433-42.
Becker, et al. Drug-induced QT interval prolongation in cancer patients. Oncol Rev., 2010; 4(4):223-232.
Benning, et al. Validation of the in vivo CD1 mouse splenocyte micronucleus test. Mutagenesis. May 1994;9(3):199-204.
Bergman, et al. Series: current issues in mutagenesis and carcinogenesis, No. 65. The genotoxicity and carcinogenicity of paracetamol: a regulatory (re)view.Mutat Res. Feb. 1, 1996;349(2):263-88.
Bessems, et al. Paracetamol (acetaminophen)-induced toxicity: molecular and biochemical mechanisms, analogues and protective approaches. Crit Rev Toxicol. Jan. 2001;31(1):55-138.
Betancourt, et al. Efficacy of ibuprofen-hydrocodone for the treatment of postoperative pain after periodontal surgery. J Periodontol. Jun. 2004;75(6):872-6.
Blecharz-Klin, et al. Developmental exposure to paracetamol causes biochemical alterations in medulla oblongata. Environ Toxicol Pharmacol. Sep. 2015;40(2):369-74. doi: 10.1016/j.etap.2015.07.001. Epub Jul. 4, 2015.
Bovbjerg, et al. An experimental analysis of classically conditioned nausea during cancer chemotherapy. Psychosom Med. Nov.-Dec. 1992;54(6):623-37.
Bruera, et al. The Edmonton Symptom Assessment System (ESAS): a simple method for the assessment of palliative care patients. J Palliat Care. 1991 Summer;7(2):6-9.
Burke, et al. Evaluation of pyrazole and ethanol induced S9 fraction in bacterial mutagenicity testing. Mutagenesis. Jan. 1994;9(1):23-9.
Chang, et al. Validation of the Edmonton Symptom Assessment Scale. Cancer. May 1, 2000;88(9):2164-71.
Chapin, et al. Reproductive assessment by continuous breeding: evolving study design and summaries of ninety studies. Environ Health Perspect. Feb. 1997;105 Suppl 1:199-205.
Chen, et al. Design and analysis for drug abuse potential studies: issues and strategies for implementing a crossover design. Dia J. 2007; 41:481-489.
Cherny. Opioid analgesics: comparative features and prescribing guidelines. Drugs. May 1996;51(5):713-37.
Chow, et al. Chapter 4: Statistical Methods for Average Bioavailability. Design and Analysis of Bioavailability and Bioequivalence Studies. 2nd Edition. Published by Marcel Dekker, 2000. p. 98. DCN 3007688.
Chow, et al. Chapter 6: Transformation and analysis of individual subject ratios. Design and Analysis of Bioavailability and Bioequivalence Studies. 2nd Edition. Published by Marcel Dekker, 2000. p. 161.
Cisternas, et al. Trends in medical care expenditures of US adults with arthritis and other rheumatic conditions 1997 to 2005. J Rheumatol. Nov. 2009;36(11):2531-8. doi: 10.3899/jrheum.081068. Epub Oct. 1, 2009.
Cleren, et al. Promethazine protects against 1-methyl-4-phenyl-1,2,3,6-tetrahydropyridine neurotoxicity. Neurobiol Dis. Dec. 2005;20(3):701-8. Epub Aug. 26, 2005.
Cliet, et al. In vivo micronucleus test using mouse hepatocytes. Mutat Res. Dec. 1989;216(6):321-6.
Colagiuri, et al. Patient expectancy and post-chemotherapy nausea: a meta-analysis. Ann Behav Med. Aug. 2010;40(1):3-14. doi: 10.1007/s12160-010-9186-4.
Colloca, et al. Placebo and Nocebo. In the: Textbook of Clinical Pain Management 2E, edited by Rice A, Howard R, Justins D, Miaskowski C, Newton-John T. Hodder Arnold, Practice and Procedures. London NW1 3BH, 2008, 499-513.
Colloca, et al. The role of learning in nocebo and placebo effects. Pain. May 2008;136(1-2):211-8. doi: 10.1016/j.pain.2008.02.006. Epub Mar. 26, 2008.
Cone, et al. Comparative metabolism of hydrocodone in man, rat, guinea pig, rabbit, and dog. Drug Metab Dispos. Jul.-Aug. 1978;6(4):488-93.
Cone, et al. Prescription opioids. II. Metabolism and excretion patterns of hydrocodone in urine following controlled single-dose administration. J Anal Toxicol. Oct. 2013;37(8):486-94. doi: 10.1093/jat/bkt066. Epub Aug. 14, 2013.
Connolly, et al. Alpha 4-2 beta 2 and other nicotinic acetylcholine receptor subtypes as targets of psychoactive and addictive drugs. Br J Pharmacol. Mar. 1992;105(3):657-66.
Cooper, et al. A model to evaluate mild analgesics in oral surgery outpatients. Clin Pharmacol Ther. Aug. 1976;20(2):241-50.
Cooper, et al. Ibuprofen and acetaminophen in the relief of acute pain: a randomized, double-blind, placebo-controlled study. J Clin Pharmacol. Nov. 1989;29(11):1026-30.
Da Silva, et al. Acute brain damage induced by acetaminophen in mice: effect of diphenyl diselenide on oxidative stress and mitochondrial dysfunction. Neurotox Res. Apr. 2012;21(3):334-44. doi: 10.1007/s12640-011-9288-1. Epub Nov. 12, 2011.
Dagenais, et al. Systematic review of the prevalence of radiographic primary hip osteoarthritis. Clin Orthop Relat Res. Mar. 2009;467(3):623-37. doi: 10.1007/s11999-008-0625-5. Epub Nov. 27, 2008.
Daniels, et al. The analgesic efficacy of valdecoxib vs. oxycodone/acetaminophen after oral surgery. J Am Dent Assoc. May 2002;133(5):611-21; quiz 625.
Darwish, et al. Dose proportionality of a hydrocodone extended-release tablet formulated with abuse-deterrence technology. Clin Drug Investig. May 2015;35(5):291-7. doi: 10.1007/s40261-015-0280-z.
Darwish, et al. Single- and multiple-dose pharmacokinetics of a hydrocodone bitartrate extended-release tablet formulated with abuse-deterrence technology in healthy, naltrexone-blocked volunteers. Clin Ther. Feb. 1, 2015;37(2):390-401. doi: 10.1016/j.clinthera.2014.11.014. Epub Dec. 24, 2014.
Davis, et al. Species differences in hepatic glutathione depletion, covalent binding and hepatic necrosis after acetaminophen. Life Sci. Jun. 1, 1974;14(11):2099-109.
Desjardins, et al. A randomized controlled study comparing rofecoxib, diclofenac sodium, and placebo in post-bunionectomy pain. Curr Med Res Opin. Oct. 2004;20(10):1523-37.
Desjardins, et al. A single preoperative oral dose of valdecoxib, a new cyclooxygenase-2 specific inhibitor, relieves post-oral surgery or bunionectomy pain. Anesthesiology. Sep. 2002;97(3):565-73.
Desjardins, et al. Analgesic efficacy of preoperative parecoxib sodium in an orthopedic pain model. J Am Podiatr Med Assoc. May-Jun. 2004;94(3):305-14.
Devalia, et al. Dissociation of cell death from covalent binding of paracetamol by flavones in a hepatocyte system. Biochem Pharmacol. Dec. 1, 1982;31(23):3745-9.
Devarakonda, et al. Comparison of single-dose and multiple-dose pharmacokinetics between two formulations of hydrocodone bitartrate/acetaminophen: immediate-release versus biphasic immediate-release/extended release. J Pain Res. Sep. 9, 2015;8:607-18. doi: 10.2147/JPR.S79578. eCollection 2015.
Dipasquale, et al. Post nidatory action of various compounds representing several pharmacological classes. Res Commun Chem Pathol Pharmacol. Apr. 1974;7(4):701-14.
Dunn, et al. Genotoxicity of analgesic compounds assessed by an in vitro micronucleus assay. Mutat Res. Nov. 1987;189(3):299-306.
Farrar, et al. Clinically important changes in acute pain outcome measures: a validation study. J Pain Symptom Manage. May 2003;25(5):406-11.
FDA Draft Guidance for Industry. Assessment of abuse potential of drugs, 2010.
FDA Monograph for Phenergan, Revised Jul. 2005; http://www.drugs.com/pro/phenergan.html; accessed Feb. 19, 2014.

(56) References Cited

OTHER PUBLICATIONS

FDA Monograph for Vicoprofen; Revised Oct. 2009; http://www.drugs.com/pro/vicoprofen.html; accessed Feb. 19, 2014.
Fendrick, et al. Self-selection and use patterns of over-the-counter omeprazole for frequent heartburn. Clin Gastroenterol Hepatol. Jan. 2004;2(1):17-21.
Ford. Soft-tissue bunionectomy in podiatric surgery. Clin Podiatr Med Surg. Jan. 1991;8(1):63-70.
Fricke, et al. A double-blind, single-dose comparison of the analgesic efficacy of tramadol/acetaminophen combination tablets, hydrocodone/acetaminophen combination tablets, and placebo after oral surgery. Clin Ther. Jun. 2002;24(6):953-68.
Gan, et al. A consensus panel identification of risk factors for PONV. Anesth. 2002; 97:A19.
Gan, et al. Consensus guidelines for managing postoperative nausea and vomiting. Anesth Analg. Jul. 2003;97(1):62-71, table of contents.
Gan, et al. Risk factors for postoperative nausea and vomiting. Anesth Analg. Jun. 2006;102(6):1884-98.
Gordon, et al. Activation of P-glycoprotein efflux transport ameliorates opioid CNS effects without diminishing analgesia. Drug Disc Today: Therap Strat 2009; 6:97-103.
Gotzsche. Reporting of outcomes in arthritis trials measured on ordinal and interval scales is inadequate in relation to meta-analysis. Ann Rheum Dis. Apr. 2001;60(4):349-52.
Gotzsche. Sensitivity of effect variables in rheumatoid arthritis: a meta-analysis of 130 placebo controlled NSAID trials. J Clin Epidemiol. 1990;43(12):1313-8.
Griffiths, et al. Principles of initial experimental drug abuse liability assessment in humans. Drug Alcohol Depend. Jun. 5, 2003;70(3 Suppl):S41-54.
Hays, et al. The RAND 36-Item Health Survey 1.0. Health Econ. Oct. 1993;2(3):217-27.
Hersh, et al. Ibuprofen liquigel for oral surgery pain. Clin Ther. Nov. 2000;22(11):1306-18.
Korn, et al. Comparison of rofecoxib and oxycodone plus acetaminophen in the treatment of acute pain: a randomized, double-blind, placebo-controlled study in patients with moderate to severe postoperative pain in the third molar extraction model. Clin Ther. May 2004;26(5):769-78.
Lasagna. A plea for the 'Naturalistic' study of medicines. Eur J Clin Pharmacol. 1974;7(3):153-4.
Lasagna. The clinical measurement of pain. Ann N Y Acad Sci. Mar. 30, 1960;86:28-37.
Lasagna. The controlled clinical trial: theory and practice. J Chronic Dis. Apr. 1955;1(4):353-67.
Litkowski, et al. Analgesic efficacy and tolerability of oxycodone 5 mg/ibuprofen 400 mg compared with those of oxycodone 5 mg/acetaminophen 325 mg and hydrocodone 7.5 mg/acetaminophen 500 mg in patients with moderate to severe postoperative pain: a randomized, double-blind, placebo-controlled, single-dose, parallel-group study in a dental pain model. Clin Ther. Apr. 2005;27(4):418-29.
Malmstrom, et al. Comparison of rofecoxib and celecoxib, two cyclooxygenase-2 inhibitors, in postoperative dental pain: a randomized, placebo- and active-comparator-controlled clinical trial. Clin Ther. Oct. 1999;21(10):1653-63.
Melzack, et al. On the language of pain. Anesthesiology. Jan. 1971;34(1):50-9.
Moore, et al. Prevalence of opioid adverse events in chronic non-malignant pain: systematic review of randomised trials of oral opioids. Arthritis Res Ther. 2005;7(5):R1046-51. Epub Jun. 28, 2005.
Neogi, et al. Composite versus individual measures of disease activity in rheumatoid arthritis. J Rheumatol. Feb. 2008;35(2):185-7.
Neogi, et al. Relative responsiveness of physician/assessor-derived and patient-derived core set measures in rheumatoid arthritis trials. J Rheumatol. May 2008;35(5):757-62. Epub Apr. 15, 2008.

O'Connor, et al. Framing effects on expectations, decisions, and side effects experienced: the case of influenza immunization. J Clin Epidemiol. Nov. 1996;49(11):1271-6.
Petersson, et al. Radiographic osteoarthritis of the knee classified by the Ahlbäck and Kellgren & Lawrence systems for the tibiofemoral joint in people aged 35-54 years with chronic knee pain. Ann Rheum Dis. Aug. 1997;56(8):493-6.
Porreca, et al. Nausea and vomiting side effects with opioid analgesics during treatment of chronic pain: mechanisms, implications, and management options. Pain Med. May-Jun. 2009;10(4):654-62. doi: 10.1111/j.1526-4637.2009.00583.x. Epub Mar. 19, 2009.
Quessy. Two-stage enriched enrolment pain trials: a brief review of designs and opportunities for broader application. Pain. Jan. 2010;148(1):8-13. doi: 10.1016/j.pain.2009.10.029. Epub Nov. 25, 2009.
Registry of Toxic Effects of Chemical Substances (RTECS) Database: Hydrocodone. MDL Information Systems. Updated Dec. 2010.
Reidenberg, et al. Adverse nondrug reactions. N Engl J Med. Sep. 26, 1968;279(13):678-9.
Rodriguez, et al. Codeine/acetaminophen and hydrocodone/acetaminophen combination tablets for the management of chronic cancer pain in adults: a 23-day, prospective, double-blind, randomized, parallel-group study. Clin Ther. Apr. 2007;29(4):581-7.
Rodriguez, et al. Incidence of weak opioids adverse events in the management of cancer pain: a double-blind comparative trial. J Palliat Med. Feb. 2007;10(1):56-60.
Rush, et al. Chemically induced nephrotoxicity: role of metabolic activation. Crit Rev Toxicol. 1984;13(2):99-160.
Sanofi-Aventis. Phenergan® Tablets/Elixir Data Sheet. 2007.
Sasaki, et al. Cytogenetic effects of 60 chemicals on cultured human and Chinese hamster cells. Kromosomo. 1980; 20:574-584.
Savides, et al. Acetaminophen and its toxicity. J Appl Toxicol. Apr. 1983;3(2):96-111.
Savides, et al. The toxicity and biotransformation of single doses of acetaminophen in dogs and cats. Toxicol Appl Pharmacol. Jun. 15, 1984;74(1):26-34.
Sawaddiruk, et al. Comparison of efficacy and effectiveness between ULTRACET and tramadol/acetaminophen in acute postoperative pain after upper extremity surgery. J Med Assoc Thai. Jul. 2010;93(7):812-7.
Schachtel, et al. . A randomized, double-blind, placebo-controlled model demonstrating the topical effect of benzydamine in children with sore throat. Clin Pharmacol Ther 1996; 59:146.
Schachtel, et al. A placebo-controlled model for assaying systemic analgesics in children. Clin Pharmacol Ther. May 1993;53(5):593-601.
Schachtel, et al. Actual-use study of omeprazole magnesium. Clin Pharmacol Ther. 2000; 67:149.
Schachtel, et al. Assaying analgesic response in children: a double-blind, placebo-controlled model involving earache. Pediatr Res 1991; 29:124A.
Schachtel, et al. Caffeine as an analgeic adjuvant:a double-blind study comparing aspirin 800mg with caffeine 64mg to aspirin 800 mg and placebo in patients with sore throat. Arch Int Med. 1991; 151:733-8.
Schachtel, et al. Change in design of actual-use study assists in interpretation of study results. Abstract P11. Clin Pharmacol Ther. 2001; 69:P11.
Schachtel, et al. Gastric side effects of aspirin compared to acetaminophen and placebo in the treatment of headache. Acta Pharmacol Toxicol. 1986; 59:170.
Schachtel, et al. Pain relief in children. A placebo-controlled model. Clin Pharmacol Ther 1991; 49:154.
Schachtel, et al. Patients' criteria for meaningful relief to determine onset of action. Clin Pharmacol Ther. 2005; 77:P51.
Schachtel, et al. Rating scales for analgesics in sore throat. Clin Pharmacol Ther. Aug. 1984;36(2):151-6.
Schachtel, et al. Sore throat pain model for the evaluation of analgesics in children. J Pain and Symptom Manag 1991; 6:159.
Schachtel, et al. The Lasagna Pain Scale (LPS). Clin Pharmacol Ther. 2005; 77:93.

(56) References Cited

OTHER PUBLICATIONS

Schachtel. Analgesic agents. In: Yaffe SJ and Aranda JV, eds. Pediatric Pharmacology. Therapeutic Principles in Practice. Philadelphia: WB Saunders,1992:406-412.
Schachtel. How actual-use studies augment product development. Abstract A95. AAPS—Pharmaceutical Sciences Section, American Association of Pharmaceutical Sciences (AAPS). 1 (Suppl):A95. 1999.
Schachtel. Sore throat pain. In: Max MB, Portnoy RK, and Laska EM, eds. The Design of Analgesic Clinical Trials. (Advances in pain research and therapy; vol. 18) New York: Raven Press, 1991:393-406.
Schwinghammer, et al. Comparison of the bioavailability of oral, rectal and intramuscular promethazine. Biopharm Drug Dispos. Apr.-Jun. 1984;5(2):185-94.
Seeff, et al. Acetaminophen hepatotoxicity in alcoholics. Ann Intern Med. 1986;104:339-404.
Serratoni, et al. Promethazine protection in carbon tetrachloride liver injury. An electron microscopic study. Arch Pathol. Jan. 1969;87(1):46-51.
Severin, et al. Induction of chromosome aberrations in vivo in bone-marrow cells of mice by paracetamol. Rom J Morphol Embryol. Jul.-Dec. 1995;41(3-4):117-20.
Shang, et al. Effect of promethazine on electrophysiological action of guinea pig hearts. Chin J Pharmacol Toxicol; 28(5): 691-697.
Sharma, a, & Hamelin, B. a. (2003). Classic histamine H1 receptor antagonists: a critical review of their metabolic and pharmacokinetic fate from a bird's eye view. Current Drug Metabolism, 4(2), 105-129. doi:10.2174/1389200033489523.
Shibata, et al. Modification by analgesics of lesion development in the urinary tract and various other organs of rats pretreated with dihydroxy-di-N-propylnitrosamine and uracil. Jpn J Cancer Res. Feb. 1995;86(2):160-7.
Shuey, et al. Oxymorphone hydrochloride, a potent analgesic, is not carcinogenic in rats or mice. Toxicol Sci. Mar. 2007;96(1):162-73. Epub Nov. 30, 2006.
Siegers, et al. Relationships between hepatotoxicity and pharmacokinetics of paracetamol in rats and mice. Pharmacology. 1978;16(5):273-8.
Song, et al. Quantitation of promethazine and metabolites in urine samples using on-line solid-phase extraction and column-switching. J Chromatogr B Biomed Sci Appl. Nov. 5, 2001;763(1-2):9-20.
Stavchansky, et al. Bioequivalence and pharmacokinetic profile of promethazine hydrochloride suppositories in humans J Pharm Sci. Jun. 1987;76(6):441-5.
Stavrovskaya, et al. Clinically approved heterocyclics act on a mitochondrial target and reduce stroke-induced pathology. J Exp Med. Jul. 19, 2004;200(2):211-22.
Sullivan, et al. The pain catastrophizing scale: development and validation. Psychological Assessment, vol. 7(4), Dec. 1995, 524-532.
Szyfelbein, et al. The assessment of pain and plasma beta-endorphin immunoactivity in burned children. Pain. Jun. 1985;22(2):173-82.
Tanaka, et al. Blockade of Na+ current by promethazine in guinea-pig ventricular myocytes. Br J Pharmacol. Aug. 1992;106(4):900-5.
Taylor, et al. Pharmacokinetics of promethazine and its sulphoxide metabolite after intravenous and oral administration to man. Br J Clin Pharmacol. Mar. 1983;15(3):287-93.
Thoden, et al. Adverse non-drug reactions (ANDRs) in patients with muscle-contraction headache. Clin Pharmacol Ther. 1990; 47:149.
Tomkins, et al. Effect of cytochrome P450 2D1 inhibition on hydrocodone metabolism and its behavioral consequences in rats. J Pharmacol Exp Ther. Mar. 1997;280(3):1374-82.
Tsuruzaki, et al. Maternal consumption of antipyretic analgesics produces chromosome anomalies in F1 embryos. Teratology. 1982; 26:42A.
Urie, et al. Pharmacy education: palliative care symptom control. In:The Pharmaceutical Journal. 2000; 265:603.
Vaisman, et al. The effect of promethazine hydrochloride on bilirubin metabolism in the rat. Pediatr Res. Sep. 1976;10(9):788-91.
Walsh, et al. The relative abuse liability of oral oxycodone, hydrocodone and hydromorphone assessed in prescription opioid abusers. Drug Alcohol Depend. Dec. 1, 2008;98(3):191-202. doi: 10.1016/j.drugalcdep.2008.05.007. Epub Jul. 7, 2008.
Ward, et al. The chronic hepatic or renal toxicity of di(2-ethylhexyl) phthalate, acetaminophen, sodium barbital, and phenobarbital in male B6C3F1 mice: autoradiographic, immunohistochemical, and biochemical evidence for levels of DNA synthesis not associated with carcinogenesis or tumor promotion. Toxicol Appl Pharmacol. Dec. 1988;96(3):494-506.
Ware, et al. The MOS 36-item short-form health survey (SF-36). I. Conceptual framework and item selection. Med Care. Jun. 1992;30(6):473-83.
Weisburger, et al. Effect of acetanilide and p-hydroxyacetanilide on the carcinogenicity of N-2-fluorenylacetamide and N-hydroxy-N-2-fluorenylacetamide in mice, hamsters, and female rats. J Natl Cancer Inst. Jul. 1973;51(1):235-40.
Wesson, et al. The Clinical Opiate Withdrawal Scale (COWS). J Psychoactive Drugs. Apr.-Jun. 2003;35(2):253-9.
Whitcomb, et al. Association of acetaminophen hepatotoxicity with fasting and ethanol use. JAMA. Dec. 21, 1994;272(23):1845-50.
Whitfield, et al. Parsimonious and efficient assessment of health-related quality of life in osteoarthritis research: validation of the Assessment of Quality of Life (AQoL) instrument. Health Qual Life Outcomes. 2006; 4:19.
Wiger, et al. Effects of acetaminophen and hydroxyurea on spermatogenesis and sperm chromatin structure in laboratory mice. Reprod Toxicol. Jan.-Feb. 1995;9(1):21-33.
Williams, et al. Inhibition by acetaminophen of intestinal cancer in rats induced by an aromatic amine similar to food mutagens. Eur J Cancer Prev. Aug. 1997;6(4):357-62.
Wirth, et al. Mechanism of N-hydroxyacetylarylamine mutagenicity in the Salmonella test system: metabolic activation of N-hydroxyphenacetin by liver and kidney fractions from rat, mouse, hamster, and man. Mol Pharmacol. Jul. 1980;18(1):117-27.
Wyeth Pharmaceuticals Inc. Phenergan® Label. 2005.
Wyeth Pharmaceuticals, I. (2010). Phenergan® (promethazine HCl) Tablets and Suppositories Full Prescribing Information. http://www.accessdata.fda.gov/drugsatfda_docs/label/2004/07935s0301bl.pdf. Philadelphia, PA, Wyeth Pharmaceuticals, Inc.: 1-10.
Wyeth Pharmaceuticals, Inc. Phenergan Tablets. United States Prescribing Information (NDA 007935; drugs@fda.gov, listed PI update as of Nov. 2004) for Phenergan®-promethazine hydrochloride, tablet.
Yoon, et al. Chemical mutagenesis testing in Drosophila. IV. Results of 45 coded compounds tested for the National Toxicology Program. Environ Mutagen. 1985;7(3):349-67.
York, et al. Developmental toxicity studies in rats and rabbits with orally administered hydrocodone bitartrate (HB), USP. Reprod Toxicol. 2003; 17: 507.
Yoshida, et al. Mutagenicity of p-aminophenol in *E. coli* WP2uvrA/pKM101 and its relevance to oxidative DNA damage. Mutat Res. Jul. 8, 1998;415(1-2):139-50.
Zacny, et al. Profiling the subjective, psychomotor, and physiological effects of a hydrocodone/acetaminophen product in recreational drug users. Drug Alcohol Depend. Jun. 1, 2005;78(3):243-52. Epub Jan. 12, 2005.
Zacny, et al. Subjective, psychomotor, and physiological effects profile of hydrocodone/acetaminophen and oxycodone/acetaminophen combination products. Pain Med. May-Jun. 2008;9(4):433-43. doi: 10.1111/j.1526-4637.2007.00359.x.
Zacny, et al. Within-subject comparison of the psychopharmacological profiles of oral hydrocodone and oxycodone combination products in non-drug-abusing volunteers. Drug Alcohol Depend. Apr. 1, 2009;101(1-2):107-14. doi: 10.1016/j.drugalcdep.2008.11.013. Epub Dec. 31, 2008.
Zaman, et al. Bioequivalency and dose proportionality of three tableted promethazine products. Biopharm Drug Dispos. May-Jun. 1986;7(3):281-91.
Zenser, et al. Enzyme systems involved in the formation of reactive metabolites in the renal medulla: cooxidation via prostaglandin H synthase. Fundam Appl Toxicol. Dec. 1984;4(6):922-9.

(56) References Cited

OTHER PUBLICATIONS

Zhelev, et al. Phenothiazines suppress proliferation and induce apoptosis in cultured leukemic cells without any influence on the viability of normal lymphocytes. Phenothiazines and leukemia. Cancer Chemother Pharmacol. Mar. 2004;53(3):267-75. Epub Dec. 9, 2003.
Zimmerman, et al. Acetaminophen (paracetamol) hepatotoxicity with regular intake of alcohol: analysis of instances of therapeutic misadventure. Hepatology. Sep. 1995;22(3):767-73.
Notice of allowance dated Feb. 8, 2015 for U.S. Appl. No. 14/789,888.
Sadock, et al. Kaplan & Sadock's pocket handbook of psychiatric drug treatment 4th Ed, illustrated. Lippincott Williams & Wilkins 2005; Chapter 11.
Steyer, et al. Mehrdimensionaler Befindlichkeitsfrageboen. [Multi-dimensional well-being questionnaire] Gottingen: Hogrefe. 1997.
Interview summary dated Sep. 18, 2015 for U.S. Appl. No. 14/789,888.
Interview summary dated Oct. 2, 2015 for U.S. Appl. No. 14/789,888.
Interview summary dated Oct. 20, 2015 for U.S. Appl. No. 14/036,946.
Interview summary dated Nov. 23, 2015 for U.S. Appl. No. 14/748,614.
Interview summary dated Nov. 23, 2015 for U.S. Appl. No. 14/748,617.
Interview summary dated Nov. 24, 2015 for U.S. Appl. No. 14/244,455.
Interview summary dated Nov. 24, 2015 for U.S. Appl. No. 14/748,605.
Interview summary dated Nov. 25, 2015 for U.S. Appl. No. 14/789,883.
Navratil, H. Contribution to the study of dihydrone pectinate. Its administration in the course of anesthesia 100 observations. Rev. MRO. Toulouse. 1966, II. pp. 249-254 (in French with English translation).
Notice of allowance dated Sep. 24, 2015 for U.S. Appl. No. 14/036,946.
Notice of allowance dated Oct. 2, 2015 for U.S. Appl. No. 14/789,888.
Notice of allowance dated Nov. 4, 2015 for U.S. Appl. No. 14/789,888.
Office action dated Oct. 2, 2015 for U.S. Appl. No. 14/748,613.
Notice of allowance dated Feb. 18, 2016 for U.S. Appl. No. 14/244,455.
Notice of allowance dated Feb. 19, 2016 for U.S. Appl. No. 14/748,605.
Notice of allowance dated Feb. 18, 2016 for U.S. Appl. No. 14/748,609.
Notice of allowance dated Feb. 19, 2016 for U.S. Appl. No. 14/748,614.
Bouillon, T. et al. A model of the ventilatory depressant potency of remifentanil in the non-steady state. Anesthesiology 2003;99:779-87.
DeSchepper, H.U. et al. Opioids and the gut: pharmacology and current clinical experience. Neurogastroenterol Motil. Aug. 2004;16(4):383-94.
Holzer, P. Treatment of opioid-induced gut dysfunction. Expert Opin Investig Drugs 2007;16:181-194.
Jang, J.O. et al. Pharmacokinetic Study of Promethazine in Korean Healthy Subjects Using a Validated HPLC Method. J Appl Pharm. 2005;13:118-122.
Lalley, P.M. Mu-opioid receptor agonist effects on medullary respiratory neurons in the cat: evidence for involvement in certain types of ventilatory disturbances. Am J Physiol Regul Integr Comp Physiol. Dec. 2003;285(6):R1287-304.
Mellen, N.M., et al. Opioid-induced quantal slowing reveals dual networks for respiratory rhythm generation. Neuron. Mar. 6, 2003;37(5):821-6.
Palangio, M., et al. Dose-response effect of combination hydrocodone with ibuprofen in patients with moderate to severe postoperative pain. Clin Ther. Aug. 2000;22(8):990-1002.
Peloso, P.M., et al. Protocol TRP-CAN-1 Study Group. Analgesic efficacy and safety of tramadol/acetaminophen combination tablets (Ultracet) in treatment of chronic low back pain: a multicenter, outpatient, randomized, double blind, placebo controlled trial. J Rheumatol. Dec. 2004;31(12):2454-63.
U.S. Appl. No. 14/244,455 Notice of Allowability Mailed Mar. 8, 2016.
U.S. Appl. No. 14/789,886 Final Office Action Mailed Mar. 18, 2016.
U.S. Appl. No. 14/789,888 Notice of Allowance Mailed Apr. 5, 2016.
U.S. Appl. No. 14/789,883 Final Office Action Mailed Mar. 17, 2016.
Chang DJ, et al. Comparison of rofecoxib and a multidose oxycodone/acetaminophen regimen for the treatment of acute pain following oral surgery: a randomized controlled trial. Curr. Med. Res. Opin. 2004; 20: 939-49.
Kalso E., et al. Opioids in chronic non-cancer pain: systematic review of efficacy and safety Pain. 2004; 112: 372-80.
U.S. Appl. No. 14/748,605 Notice of Allowance Mailed May 6, 2016.
U.S. Appl. No. 14/748,609 Notice of Allowance Mailed May 3, 2016.
U.S. Appl. No. 14/244,455 Notice of Allowance Mailed May 17, 2016.

PHARMACEUTICAL COMPOSITIONS

CROSS-REFERENCE

This application claims the benefit of U.S. application Ser. No. 14/099,432, filed Dec. 6, 2013, which is a continuation of U.S. application Ser. No. 12/444,521, a national stage entry of PCT/US2007/080831 filed Oct. 9, 2007, now U.S. Pat. No. 8,653,066, which claims the benefit of U.S. Provisional Applications No. 60/850,451 filed Oct. 9, 2006, 60/921,563 filed Apr. 3, 2007, and 60/948,375 filed Jul. 6, 2007, all of which are incorporated herein by reference in their entirety.

BACKGROUND OF THE INVENTION

Available pain medications may have adverse effects such as nausea, vomiting, and skin rashes. While such medications may be effective in providing pain relief, many subjects are unable to tolerate recommended dosages needed for effective pain relief because of adverse effects. Accordingly, there remains a need for effective analgesics with reduced adverse effects within the art of analgesic compositions.

SUMMARY OF THE INVENTION

In general the invention comprises methods and compositions designed to treat a subject with a drug formulation comprising multiple active agents.

In one aspect of the invention a composition comprises, an opioid analgesic, a non-opioid analgesic agent, an agent that reduces or eliminates a adverse effect of an opioid analgesic agent and a pharmaceutically acceptable carrier or vehicle.

The invention also relates to methods for treating pain comprises administering to a subject in need thereof an effective amount of an opioid analgesic agent, a non-opioid analgesic agent and an agent that reduces or eliminates a adverse effect of an opioid analgesic agent. For example, the agent which reduces adverse effects is an anti-emetic agent or antihistamine.

The invention further relates to pharmaceutical compositions comprising from 1% to 20% by weight of an antihistamine; from 10% to 80% by weight a non-opioid analgesic; and from 1% to 20% by weight of an opioid analgesic. In a further aspect, a pharmaceutical composition comprises an opioid analgesic, a non-opioid analgesic and an antihistamine, wherein the relative ratio of said opioid analgesic, said non-opioid analgesic and said antihistamine is from 1 to 2:40 to 45:1 to 2 respectively.

The invention also relates to, pharmaceutical compositions comprising an opioid analgesic, a non-opioid analgesic and an antihistamine, which is designed to provide a plasma concentration of said antihistamine at a substantially greater rate than said opioid and said non-opioid analgesic.

In another aspect of the invention, a method of treating a subject to alleviate any condition which could benefit from administering an effective amount of a pharmaceutical composition comprising an opioid analgesic, a non-opioid analgesic and an antihistamine. In one embodiment, the condition is a adverse effect associated with administration of an opioid analgesic.

The invention further relates to methods for treating a subject suffering from or susceptible to pain, comprises administering to said subject a pharmaceutical composition comprising an effective amount of a first component which is a non-opioid analgesic, or a pharmaceutically acceptable salt thereof; a second component which is a non-opioid analgesic, or a pharmaceutically acceptable salt thereof; and an effective amount of a third component which is an antihistamine.

INCORPORATION BY REFERENCE

All publications and patent applications mentioned in this specification are herein incorporated by reference to the same extent as if each individual publication or patent application was specifically and individually indicated to be incorporated by reference.

DETAILED DESCRIPTION OF THE INVENTION

Figure 1:
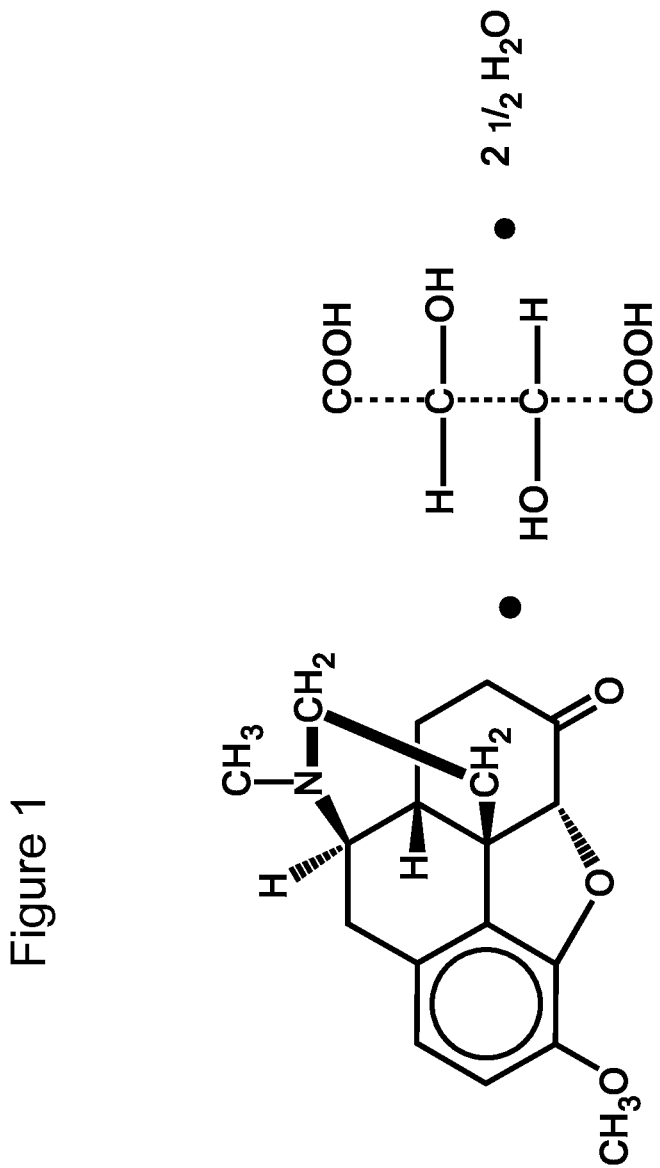
FIG. 1. illustrates the chemical structure of hydrocodone bitartrate. It is an opioid analgesic and antitussive and occurs as fine, white crystals or as a crystalline powder. The chemical name is: 4,5α-epoxy-3-methoxy-17-methylmorphinan-6-one tartrate (1:1) hydrate (2:5). The chemical formula is $C_{18}H_{21}NO_3 \cdot C_4H_6O_6 \cdot 2\frac{1}{2}H_2O$; M.W.=494.50.
Figure 2:
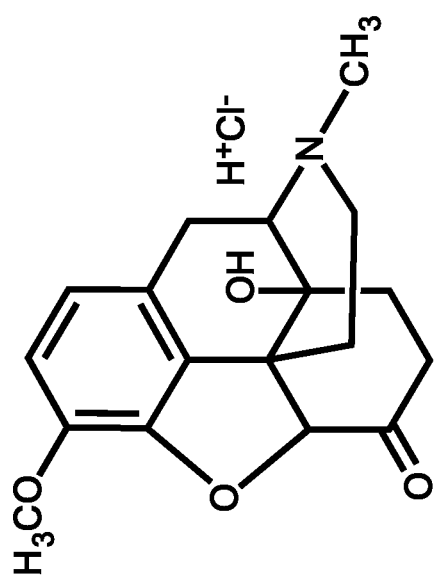
FIG. 2. illustrates the chemical structure of oxycodone hydrochloride.
Figure 3:
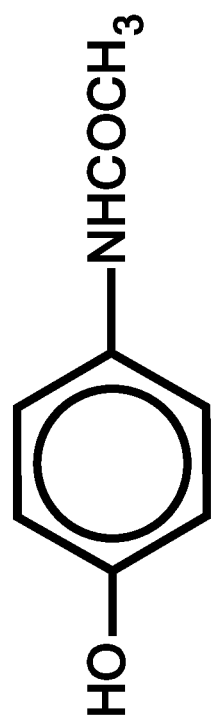
FIG. 3. illustrates the chemical structure of acetaminophen, 4'-hydroxyacetanilide. It is a slightly bitter, white odorless, crystalline powder, and a non-opioid, non-salicylate analgesic and antipyretic. The chemical formula is $C_8H_9NO_2$; M.W.=151.16.
Figure 4:
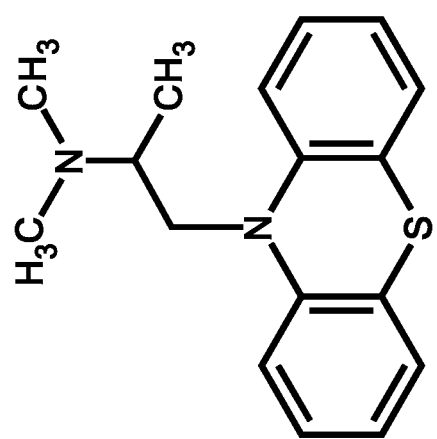
FIG. 4. illustrates the chemical structure of promethazine.

The present invention is generally directed to compositions comprising of multiple active agents that are useful as therapeutics that alleviate, abate or eliminate an adverse effect associated with opioid and/or non-opioid anagesic agents. In various embodiments of the invention a composition comprises an effective amount of two actives, an effective amount of three active agents, an effective amount of four active agents, an effective amount of five active agents or more than five active agents. An active agent is selected from various classes of drugs, including but not limited to opioid analgesics, non-opioid analgesics, decongestant, expectorant, mucus thinning drugs, antitussives, antihistamines or a combination thereof.

Various aspects of the invention are directed to compositions comprising an analgesic (e.g., one analgesic or two, three or more analgesics) and an adverse-effect-reducing active agent (e.g., an antihistamine or antiemetic). Such analgesics can include one or more opioid analgesics, or one or more non-opioid analgesics. In various further embodiments the compositions comprise an antihistamine, or an antiemetic.

In one aspect, a pharmaceutical composition is provided comprising, an effective amount of an opioid analgesic, an effective amount of non-opioid analgesic agent, and an effective amount of an agent that reduces or eliminates an adverse effect of said analgesic agents. In one embodiment, the agent that reduces or eliminates an adverse effect is an antiemetic agent or antihistamine. In further embodiments, the adverse effect reduced or eliminated is associated with an opioid analgesic. In one embodiment, the adverse effect is associated with a non-opioid analgesic.

In some embodiments, the agent which reduces or eliminates a adverse effect of an opioid analgesic agent is promethazine, dolasetron, granisetron, ondansetron, tropisetron, palonosetron, domperidone, droperidol, haloperidol, chlorpromazine, prochloperazine, metoclopramide, alizapride, cyclizine, diphenhydramine, dimenhydrinate, meclizine, hydroxyzine, cannabis, dronabinol, nabilone, midazolam, lorazepam, hyoscine, dexamethasone, trimethobenzamide, emetrol and propofol.

In one embodiment, a composition of the invention comprises a non-opioid analgesic agent which is acetaminophen or ibuprofen.

In one embodiment, the opioid analgesic agent is hydrocodone or oxycodone, or a pharmaceutically acceptable salt, thiosemicarbazone, p-nitrophenylhydrazone, o-methyloxime, semicarbazone, or bis(methylcarbamate) (each of the foregoing being an opioid analgesic agent or derivative). In a further embodiment, the opioid analgesic agent is hydrocodone bitartrate or oxycodone hydrochloride.

In one aspect of the invention, the pharmaceutical composition is in the form of a multi-layered tablet, such as in the form of a bi-layered tablet. In one embodiment, the bi-layered tablet comprises: (a) an inner, immediate-release layer that comprises the agent that reduces or eliminates a adverse effect of an opioid analgesic; and (b) an outer, controlled-release layer that comprises the agent that reduces or eliminates a adverse effect of an opioid analgesic, the opioid analgesic agent and the non-opioid analgesic agent.

In one embodiment, a pharmaceutical composition is provided comprising an opioid analgesic, a non-opioid analgesic and an antihistamine, wherein said composition is capable of providing a plasma concentration of said antihistamine at a substantially sooner than plasma concentrations of said opioid and said non-opioid analgesic are achieved post administration. For example, a pharmaceutical composition comprising three active agents—opioid analgesic, non-opioid analgesic, and antihistamine or antiemetic—will provide a plasma concentration of the latter antihistamine or aniemetic at about 1 to about 20 minutes, which is substantially faster than providing the an analgesic, which can be provided in about 30 minutes to about 12 hours.

In various embodiments, a pharmaceutical composition is provided comprising from 1% to 20% by weight of an antihistamine; from 10% to 80% by weight a non-opioid analgesic; and from 1% to 20% by weight of an opioid analgesic.

In one embodiment, the composition is capable of increasing a plasma concentration of said antihistamine in about 1 minute to about 20 minutes after administration to a subject.

In some embodiments, the antihistamine is selected from a group consisting of promethazine, dolasetron, granisetron, ondansetron, tropisetron, palonosetron, domperidone, droperidol, haloperidol, chlorpromazine, prochloperazine, metoclopramide, alizapride, cyclizine, diphenhydramine, dimenhydrinate, meclizine, hydroxyzine, cannabis, dronabinol, nabilone, midazolam, lorazepam, hyoscine, dexamethasone, trimethobenzamide, emetrol and propofol.

In one aspect of the invention, a method is provided for treating a subject in need thereof, comprising administering to a subject in need thereof an effective amount of a pharmaceutical composition comprising an opioid analgesic agent, a non-opioid analgesic agent and an agent which reduces or eliminates a adverse effect of said analgesic agents.

In one embodiment, a method is provided for treating a subject suffering from or susceptible to pain, comprising administering to said subject a pharmaceutical composition comprising an effective amount of a first agent which is a non-opioid analgesic, or a pharmaceutically acceptable salt thereof; an effective amount of a second agent which is a non-opioid analgesic, or a pharmaceutically acceptable salt thereof; and an effective amount of a third agent which reduces a adverse effect associated with said analgesics.

In some embodiments, the agent for reducing or eliminating a adverse effect is promethazine, dolasetron, granisetron, ondansetron, tropisetron, palonosetron, domperidone, droperidol, haloperidol, chlorpromazine, prochloperazine, metoclopramide, alizapride, cyclizine, diphenhydramine, dimenhydrinate, meclizine, hydroxyzine, cannabis, dronabinol, nabilone, midazolam, lorazepam, hyoscine, dexamethasone, trimethobenzamide, emetrol or propofol.

The pharmaceutical composition can be in any form disclosed herein, such as a multi-layered tablet.(e.g., a bi-layered tablet). In one embodiment, the multi-layered tablet is a bi-layered tablet that comprises: (a) an outer, immediate-release layer that comprises an agent which reduces or eliminates a adverse effect of an opioid analgesic; and (b) an inner, controlled release layer that comprises, an opioid analgesic agent and a non-opioid analgesic agent.

adverse effect. In one embodiment, the agent (e.g., promethazine) reducing or eliminating adverse effects is released at a substantially greater rate than an opioid or non-opioid analgesic comprised in a pharmaceutical composition of the invention, as further described herein. For example, a plasma concentration of the agent that reduces or eliminates an adverse effect of an opioid analgesic is achieved in about 1 minute to about 20 minutes, as compared to an analgesic plasma concentration provided in about 30 minutes to about 8 hours. In various embodiments, the pharmaceutical composition of the invention comprises an agent that reduces or eliminates an adverse effect which agent is released in at least about 1 minute to at least about 20 minutes. In one embodiment, such an agent is an antihistamine or antiemetic. In various embodiments, such an agent is promethazine, dolasetron, granisetron, ondansetron, tropisetron, palonosetron, domperidone, droperidol, haloperidol, chlorpromazine, prochloperazine, metoclopramide, alizapride, cyclizine, diphenhydramine, dimenhydrinate, meclizine, hydroxyzine, cannabis, dronabinol, nabilone, midazolam, lorazepam, hyoscine, dexamethasone, trimethobenzamide, emetrol or propofol.

In one embodiment, a pharmaceutical composition comprises an opioid analgesic agent, a non-opioid analgesic agent, and an agent useful for preventing and/or suppressing an adverse effect associated with the opioid and/or non-opioid analgesic. An adverse effect of an opioid and/or non-opioid analgesic includes but is not limited to nausea, vomiting, other gastric upsets, skin rashes, allergic reactions such as swelling, difficulty breathing, closing of throat, abdominal pain, unusual bleeding or bruising and skin rashes or skin rashes. In one embodiment, an averse effect(s) reduced or eliminated is associated with an opioid analgesic including but not limited to nausea, vomiting, constipation or a combination thereof.

In a further embodiment, the opioid analgesic agent is, for example, hydrocodone, oxycodone or fentanyl; the non-opioid analgesic agent is, for example, acetaminophen, ibuprofen, ketaprofen, naproxen, or aspirin; and the agent useful for preventing and/or suppressing a adverse effect is, for example, an antihistamine such as promethazine.

In another embodiment a composition comprises an analgesic agent, an antitussive agent, and an agent useful for preventing and/or suppressing a adverse effect of the analgesic agent and/or the antitussive agent. Of course, under some circumstances an antitussive is also an analgesic.

Thus in some embodiments the composition comprises acetaminophen, hydrocodone or oxycodone; the antitussive agent is, for example, dikasetron, domperidone, meclizine, dronabinol, a benzodiazepine, an anticholinergic, hydrocodone or oxycodone; the agent useful for preventing and/or suppressing adverse effect is, for example, an antihistamine such as promethazine.

Another embodiment of the invention is directed to a pharmaceutical composition, comprising an opioid analgesic agent, an non-opioid analgesic agent, and an antiemetic agent.

In a further embodiment of this invention, the opioid analgesic agent is, for example, hydrocodone, oxycodone; the non-opioid analgesic agent is, for example, acetaminophen, ibuprofen, ketaprofen, naproxen, or aspirin; the antiemetic agent is, for example 5-$HT_3$ receptor antagonists, a dopamine antagonist, an antihistamine, a cannabinoid, benzodiazepines, an anticholinergic, wherein all or less than all of the total amount of the antimetic agent is formulated for immediate release.

Another embodiment of this invention is directed to methods for the treatment of pain, comprising administering an effective amount of an opioid analgesic agent, a non-opioid analgesic agent and an agent useful for preventing and/or suppressing, reducing or eliminating a adverse effect of the opioid analgesic agent to a subject in need thereof. The methods allow for use of analgesics in populations at risk of adverse effect such as nausea, vomiting, other gastric upsets, skin rashes, allergic reactions such as swelling, difficulty breathing, closing of throat, abdominal pain, unusual bleeding or bruising and skin rashes. The opioid analgesics include, for example, hydrocodone, hydrocodone bitartrate, pharmaceutically acceptable salts and complexes of hydrocodone, oxycodone, oxycodone HCl, pharmaceutically acceptable salts and complexes of oxycodone. The non-opioid analgesics include, for example, acetaminophen, ibuprofen, ketaprofen, naproxen, or aspirin. The agents are useful for reducing or eliminating adverse effectadverse effects, such as, for example, promethazine, promethazine analogue, pharmaceutically acceptable salts and complexes of promethazine, or combinations of these compounds.

In one aspect of the invention, the pharmaceutical composition comprises an opioid analgesic, a non-opioid analgesic and an antihistamine, wherein said composition provides a plasma concentration of said antihistamine at a substantially greater rate than said opioid and said non-opioid analgesic. In one embodiment the antihistamine is formulated for immediate-release. In another embodiment the opioid analgesic and/or the non-opioid analgesic is/are formulated for controlled-release. In one embodiment the composition is capable of increasing a plasma concentration of said antihistamine immediately after administration to a subject. In this embodiment increased a plasma concentration of said antihistamine occurs from about 1 minute to about 20 minutes after administration.

Another aspect of the invention comprises a method of treating a subject to alleviate pain, comprising administering an effective amount of a pharmaceutical composition comprising an opioid analgesic, a non-opioid analgesic and an antihistamine. In one embodiment, the antihistamine is formulated for immediate release.

In various embodiments, a dosage form of the invention provides an increased plasma concentration of said antihistamine occurs from about 1 minute to about 20 minutes after administration, such as about 1 min, 2 min, 3 min, 4 min, 5 min, 6 min, 7 min, 8 min, 9 min, 10 min, 11 min, 12 min, 13 min, 14 min, 15 min, 16 min, 17 min, 18min, 19 min, 20 min, 21 min, 22 min, 23 min, 24 min, 25 min. In some embodiments, the release rate occurs at substantially faster as compared to release rates for the analgesic agents. Therefore, after administration to a subject, the antihistamine (e.g., promethazin dolasetron, granisetron, ondansetron, tropisetron, palonosetron, domperidone, droperidol, haloperidol, chlorpromazine, prochloperazine, metoclopramide, alizapride, cyclizine, diphenhydramine, dimenhydrinate, meclizine, hydroxyzine, cannabis, dronabinol, nabilone, midazolam, lorazepam, hyoscine, dexamethasone, trimethobenzamide, emetrol and propofol) is released and a plasma concentration of an antihistamine is provided before release of the opioid and/or non-opioid analgesic.

In some embodiments, a dosage form of the invention provides a plasma concentration of said opioid analgesic and/or said non-opioid analgesic occurs from about 1 hour to about 4 hours after administration, such as about 1 hr, 1.2 hrs, 1.4 hrs, 1.6 hrs, 1.8 hrs, 2.0 hrs, 2.2 hrs, 2.4 hrs, 2.6 hrs, 2.8 hrs, 3.0 hrs, 3.2 hrs, 3.4 hrs, 3.6 hrs, 3.8 hrs, 4.0 hrs, 5.0 hrs, 6.0 hrs, 7.0 hrs, 8.0 hrs, 9.0 hrs, 10.0 hrs, 11.0 hrs, 12.0 hrs, 13.0 hrs, 14.0 hrs, 15.0 hrs, 16.0 hrs, 17.0 hrs, 18.0 hrs, 19.0 hrs, 20.0 hrs, 21.0 hrs, 22.0 hrs, 23.0 hrs, or 24.0 hrs. In further embodiments, the opioid or non-opioid analgesic are present from about 1 hour to 24 hour, 1 day to 30 days, including but not limited to 1, 2, 3, 4, 5, 6, 7, 8, 9, 10, 12, 12, 13, 14, 15, 16, 17, 18, 19, 20, 21, 22, 23, 24, 25, 26, 27, 28, 29 or 30 days. For example, administration of dosage compositions can be effected through patch delivery systems which are known.

Another aspect of the invention comprises a method of treating a subject to alleviate a condition comprising administering a therapeutically effective amount of a pharmaceutical composition comprising an opioid analgesic, a non-opioid analgesic and an antihistamine. In one embodiment, the antihistamine is formulated for immediate release.

In another embodiment, a plasma concentration of said antihistamine occurs from about 1 minute to about 20 minutes after administration. In an additional embodiment, a plasma concentration of an opioid analgesic and/or non-opioid analgesic is achieved from about 1 hour to about 8 hours after administration.

In one embodiment subjects receiving opioid analgesics and acetaminophen concomitantly with, antihistamines, antipsychotics, antianxiety agents, or other CNS depressants is given a reduced dosage of one or more agents to prevent or ameliorate any additive effects, such as CNS depression. In another embodiment the dosage of one or more of the agents is adjusted according to the severity of the pain and the response of the subject.

In subjects with terminal diseases or chronic conditions pain management can be of a primary concern to the subject's quality of life. In some of these subjects tolerance to opioid analgesics can develop with continued use. In one embodiment, adjustments are made to the amounts or time release characteristics of the components in a composition, comprising an opioid analgesic, a non-opioid analgesic and an antihistamine. In this embodiment the adjustments are designed to provide pain relief to a subject with tolerance to opioid analgesics. In one embodiment the amount of the opioid analgesic may be increased in the composition to be administered to a subject. In another embodiment the time release characteristics of the opioid analgesic may be adjusted so as to change the ratio of immediate-release opioid analgesic to controlled-release opioid analgesic.

In one embodiment of the present invention, the pharmaceutical compositions comprises: hydrocodone in a dosage range of between about 1.0 mg to about 15 mg or oxycodone in a dosage range of between about 1.0 mg to about 200 mg; acetaminophen in a dosage range of between about 200 mg to about 600 mg; and, promethazine in a dosage range of between about 0.5 mg to about 60.0 mg.

In another embodiment of the present invention, the pharmaceutical compositions comprise about 7.5 mg of hydrocodone, about 325 mg of acetaminophen, and about 12.5 mg of promethazine.

In another embodiment of the present invention, the pharmaceutical compositions comprise about 7.5 mg of oxycodone, about 325 mg of acetaminophen, and about 12.5 mg of promethazine.

In another embodiment of the present invention, the pharmaceutical compositions comprise an effective amount of hydrocodone or oxycodone HCl, an effective amount of acetaminophen, and an effective amount of promethazine in a single, oral pill or tablet form having dosage levels that can be safely doubled for combating severe pain.

In a further embodiment of the present invention, all or less than all of the total amount of the promethazine is formulated for immediate release into the subject's blood stream.

In a further embodiment of the present invention, all or less than all of the total amount of the hydrocodone or oxycodone is formulated for controlled-release into the subject's body.

In various embodiments of the present invention, the agents are formulated as oral dosage forms, inhalations, nasal sprays, patches, absorbing gels, liquids, liquid tannates, suppositories, injections, I.V. drips, other delivery methods, or a combination thereof to treat subjects.

In another embodiment of the present invention, the agents are formulated as single oral dosage forms such as tablets, capsules, cachets, soft gelatin capsules, hard gelatin capsules, extended release capsules, tannate tablets, oral disintegrating tablets, multi-layer tablets, beads, liquids, oral suspensions, chewable lozenges, oral solutions, oral syrups, sterile packaged powder including pharmaceutically-acceptable excipients, other oral dosage forms, or a combination thereof.

In another embodiment of the present invention, the pharmaceutical compositions comprise an agent in immediate release, quick release, controlled release, sustained release, extended release, other release formulations or patterns, or a combination thereof.

In one aspect, a composition of the invention comprises three active agents each of which is selected from a decongestant, an antitussive, an expectorant, a mucus thinning drugs, an analgesic and an antihistamine. For example, in one embodiment an agent is an antitussive such as, e.g., codeine, dihydrocodeine, hydrocodone, dextromethorphan and a pharmaceutically acceptable salt thereof; another agent is a decongestant such as, e.g., phenylephrine, pseudoephedrine and a pharmaceutically acceptable salt thereof, and another agent is an expectorant. One will recognize that an active agent may fit into more than one category (e.g., hydrocodone is an antitussive and opioid analgesic).

In another embodiment, a composition of the invention comprises an effective amount of an opioid analgesic (e.g., hydrocodone or oxycodone), a non-opioid analgesic (e.g., acetaminophen or ibuprofen), and an antihistamine (e.g., promethazine). In a further embodiment, the composition comprises an effective amount of hydrocodone, acetaminophen and promethazine. In yet a further embodiment, the composition comprises an effective amount of oxycodone, acetaminophen and promethazine.

In any of the embodiments disclosed herein, a composition of the invention can be administered using one or more different dosage forms which are further described herein.

In other aspects of the invention, a composition of the invention is administered in various dosage forms. For example, a composition comprising multiple active agents can be administered in solid, gel, patch or liquid form. Such dosage forms are further described herein. Examples of such dosage forms are known, such as tablet forms disclosed in U.S. Pat. Nos. 3,048,526, 3,108,046, 4,786,505, 4,919,939, 4,950,484; gel forms disclosed in U.S. Pat. Nos. 4,904,479, 6,482,435, 6,572,871, 5,013,726; patches for delivery of pharmaceutical compositions such as disclosed in U.S. Pat. Nos. 5,741,510, 4,624,665, 4,626,539, 4,834,978, 6,469,227, 5,919,479, 6,261,595, 6,303,142, 6,341,387, 6,465,006, 6,613,350, 6,780,426, 7,094,228, 6,756,053; capsule forms disclosed in U.S. Pat. Nos. 4,800,083, 4,532,126, 4,935,243, 6,258,380; liquid forms disclosed in U.S. Pat. Nos. 4,625,494, 4,478,822, 5,610,184; or I.V. forms disclosed in U.S. Pat. Nos. 4,871,353, 4,925,444, 5,484,406; each of which is incorporated herein by reference in its entirety.

In other aspects of the invention, a composition of the invention is administered at various dosages and/or has various release rates (e.g., controlled release or immediate release).

Immediate release refers to the release of an active agent substantially immediately upon administration. In one embodiment, immediate release results in dissolution of an agent within 1-20 minutes after entering the stomach. Dissolution can be of all or less than all of the active. For example, dissolution of 100% of an agent (antihistamine or antiemetic) can occur in the prescribed time. Alternatively, dissolution of less than all of the agent can occur in about 1 minute to about 20 minutes (e.g., dissolution of about 70%, about 75%, about 80%, about 85%, about 90%, about 91%, about 92%, about 93%, about 94%, about 95%, about 96%, about 97%, about 98%, about about 99%, about 99.5% or 99.9% of an agent).

In another embodiment, immediate release occurs when there is dissolution of an agent within 1-20 minutes after administration. In another embodiment, immediate release results in substantially complete dissolution within about 1 hour following administration.

In various embodiments, immediate release occurs when there is dissolution of an agent within 1-20 minutes after administration. Dissolution can be in a subject's stomach and/or intestine. In another embodiment, immediate release results in complete or less than complete dissolution within about 1 hour following administration to a subject. In another embodiment, immediate release results in complete or less than complete dissolution within about 1 hour following rectal administration Immediate release components can also be referred to as instant release. When used in association with the dissolution profiles discussed herein, the term "immediate release" refers to wherein all or less than all of the total amount of a dosage form is dissolved. In some embodiments, immediate release is through inhalation, such that dissolution occurs in a subject's lungs, as further described herein. Dissolution of less than all of an active includes but is not limited to dissolution of about 50%, 60%, 70%, 80%, 85%, 90%, 95%, 97%, 98%, 99%, 99.1%, 99.2%, 99.35, 99.4%, 99.5%, 99.6%, 99.7%, 99.8% or 99.99% of the active.

Controlled-release, or sustained-release, refers to the release of an agent such as a drug or drug component from a composition or dosage form in which the agent is released according to a desired profile over an extended period of time. In one embodiment, controlled-release results in dissolution of an agent within 20-180 minutes after entering the stomach. In another embodiment, controlled-release occurs when there is dissolution of an agent within 20-180 minutes after being swallowed. In another embodiment, controlled-release occurs when there is dissolution of an agent within 20-180 minutes after entering the intestine. In another embodiment, controlled-release results in substantially complete dissolution after at least 1 hour following administration. In another embodiment, controlled-release results in substantially complete dissolution after at least 1 hour following oral administration. In another embodiment, controlled-release results in substantially complete dissolution after at least 1 hour following rectal administration. For example, controlled release compositions allow delivery of an agent to a subject over an extended period of time according to a predetermined profile. Such release rates can provide therapeutically effective levels of agent for an extended period of time and thereby provide a longer period of pharmacologic or diagnostic response as compared with conventional rapid release dosage forms. Such longer periods of response provide for many inherent benefits that are not achieved with immediate release dosages.

In using analgesics for treatments of chronic pain, controlled release formulations can be preferred over conventional short-acting formulations. When used in association with the dissolution profiles discussed herein, the term "controlled-release" refers to wherein all or less than all of the total amount of a dosage form, made according to the present invention, delivers an active agent over a period of time greater than 1 hour.

When present in a controlled-release oral dosage form, the compositions of the present invention can be dosed at a substantially lower daily dosage level than conventional immediate release products. At comparable daily dosage levels, the controlled release oral solid dosage forms can provide greater in pain relief than conventional immediate release products.

Combination Formulations

Various aspects of the invention are directed to compositions comprising an effective amount of an analgesic and an active agent that is useful for reducing an adverse effect associated with such one or more opioid analgesics, and/or one or more non-opioid analgesic. Such additional active agents include anitemetics and antihistamines. In some embodiments, the analgesics are opioid or non-opioid analgesics (e.g., hydrocodone or oxycodone and acetaminophen). In a further embodiment, the active agent which reduces adverse effects of such analgesics is promethazine.

In one embodiment, a pharmaceutical composition of the invention, by reducing adverse effects associated with an opioid and/or non-opioid analgesic allows for higher dosages for said analgesics in the pharmaceutical composition. For example, in a subject who could not otherwise tolerate a certain dosage of an opioid analgesic, a pharmaceutical composition of the invention comprising an opioid analgesic, a non-opioid analgesic and promethazine, will reduce the adverse effects (e.g. nausea, vomiting) associated with the analgesic, thus allowing for increased dosages to be administered. Furthermore, administration would be through a single composition.

In various embodiments, the analgesic agent of the multidrug composition comprises, an opioid analgesic such as hydrocodone, oxycodone, morphine, diamorphine, codeine, pethidine, alfentanil, buprenorphine, butorphanol, codeine, dezocine, fentanyl, hydromorphone, levomethadyl acetate, levorphanol, meperidine, methadone, morphine sulfate, nalbuphine, oxycodone, oxymorphone, pentazocine, propoxyphene, remifentanil, sufentanil, or tramadol; and an opioid an antagonists such as nalmefene, naloxone, or naltrexone. The composition can further comprise antitussives such as codeine or dextromethorphan.

In some embodiments, a composition of the invention comprises an opioid and non-opioid analgesic such as: codeine/acetaminophen, codeine/aspirin, hydrocodone/acetaminophen, hydrocodone/ibuprofen, oxycodone/acetaminophen, oxycodone/aspirin, or propoxyphene/aspirin or acetaminophen.

Therefore, in some embodiments, a composition comprises an analgesic and an active agent useful for reducing or eliminating adverse effects, such as an antihistamine (e.g., promethazine) and/or an antiemetic, as described herein.

In other embodiments the composition comprises an opioid, a non-opioid analgesic, and an antihistamine (e.g., promethazine).

For example, in one embodiment, a composition comprises an opioid and/or non-opioid analgesic and promethazine. In further embodiments, the composition further comprises an anti-emetic. In yet further embodiments, one or more additional adverse-effect-reducing active agents can be administered separately (concurrently, before, after, administration of a multi-drug composition). In addition, any of the compositions of the invention, can comprise a non-opioid analgesic or an opioid analgesics.

Examples of non-opioid analgesics useful in the compositions of the invention include but are not limited to acetaminophen; a non-steroidal anti-inflammatory drug (NSAID) such as a salicylate (including, for example, amoxiprin, benorilate, choline magnesium salicylate, diflunisal, faislamine, methyl salicylate, magnesium salicylate), an arylalkanoic acid (including, for example, diclofenac, aceclofenac, acemetacin, bromfenac, etodolac, indometacin, nabumetone, sulindac, tolmetin), a profen (including, for example, ibuprofen, carprofen, fenbuprofen, flubiprofen, ketaprofen, ketorolac, loxoprofen, naproxen, suprofen), a fenamic acid (including, for example mefenamic acid, meclofenamic acid), an oxicam (including, for example, piroxicam, lomoxicam, meloxicam, tenoxicam), a pyrazolidine derivative (including, for example, phenylbutazone, azapropazone, metamizole, oxyphenbutazone, sulfinprazone);and a synthetic drug having narcotic properties such as tramadol.

Each agent is useful as its free base, where applicable or its pharmaceutically acceptable salt, prodrug, analog and complex. Pharmaceutically acceptable salts include bitartrate, bitartrate hydrate, hydrochloride, p-toluenesulfonate, phosphate, sulfate, trifluoroacetate, bitartrate hemipentahydrate, pentafluoropropionate, hydrobromide, mucate, oleate, phosphate dibasic, phosphate monobasic, acetate trihydrate, bis(heptafuorobutyrate), bis(pentaflu oropropionate), bis (pyridine carboxylate), bis(trifluoroacetate), chlorhydrate, and sulfate pentahydrate . In one embodiment the agent is hydrocodone, a pharmaceutically acceptable salt or its thiosemicarbazone, p-nitrophenylhydrazone, o-methyloxime, semicarbazone, or bis(methylcarbamate). In another embodiment the agent is oxycodone, a pharmaceutically acceptable salt or its thiosemicarbazone, p-nitrophenylhydrazone, o-methyloxime, semicarbazone, or bis(methylcarbamate). In a further embodiment the agent is acetaminophen, a pharmaceutically acceptable salt or its thiosemicarbazone, p-nitrophenylhydrazone, o-methyloxime, semicarbazone, or bis(methylcarbamate). In another embodiment an agent is promethazine, a pharmaceutically acceptable salt or its thiosemicarbazone, p-nitrophenylhydrazone, o-methyloxime, semicarbazone, or bis(methylcarbamate).

The agent useful for treating a subject, such as by preventing or alleviating an adverse effect includes, for example, an antihistamine including a histamine agonist and an antagonist which is classified according to receptor subtype. H1 agonists or partial agonists include 2-(m-fluorophenyl)-histamine, and H1 antagonists include chlorpheniramine, scopolamine, mepyramine, terfenadine, astemizole, and triprolidine.

Further antagonists (which may be further classified by their chemical structures) include the ethanolamines carbinoxamine, dimenhydrinate, diphenhydramine, and doxylamine; the ethylaminediamines pyrilamine and tripelennamine; the piperazine derivatives dydroxyzine, cyclizine, fexofenadine and meclizine; the alkylamines brompheniramine and chlorpheniramine; and miscellaneous antagonists cyproheptadine, loratadine, cetrizine. H2 agonists include dimaprit, impromidine, and amthamine; and H2 antagonists (useful in the treatment of gastric acid secretion) include cimetidine, ranitidine, nizatidine, and famotidine; H3 agonists include R-alpha-methylhistamine, imetit, and immepip and H3 antagonists include thioperamide, iodophenpropit, and clobenpropit; and H4 agonists include clobenpropit, imetit, and clozapine and H4 antagonists include thioperamide. The agent useful for preventing or suppressing a adverse effect can also include an H1 blocker, such as azelastine, brompheniramine, buclizine, carbinoxamine, cetrizine, chlorpheniramine, clemastine, cyclizine, cyproheptadine, desloratidine, dimenhydrinate, diphenhydramine, emedastine, fexofenadine, hydroxyzine, ketotifen, levocabastine, loratadine, meclizine, olopatadine, phenindamine, and promoathazine.

In various embodiments of compositions comprising two, three, four, five or more active agents, at least one of the active agents is an antihistamine. In a further embodiment, the antihistamine is promethazine. In yet further embodiments, the promethazine is formulated for immediate release, controlled-release, delayed release or a combination thereof (e.g., some dosage amount for immediate release some dosage controlled/delayed release).

The compositions can comprise an antiemetic agent including, for example, promethazine, dolasetron, granisetron, ondansetron, tropisetron, palonosetron, domperidone, droperidol, haloperidol, chlorpromazine, prochloperazine, metoclopramide, alizapride, cyclizine, diphenhydramine, dimenhydrinate, meclizine, hydroxyzine, cannabis, dronabinol, nabilone, midazolam, lorazepam, hyoscine, dexamethasone, trimethobenzamide, emetrol, propofol, or the like.

The composition can comprise an antitussive agent including, for example, dextromethorphan, noscapine, ethyl morphine, codeine, camphor, menthol, theobromine, guaifenesin, or the like.

Therefore in various embodiments of the invention, a composition comprises at least two analgesics; and one antihistamine or antiemetic. For example, in one embodiment, a composition comprises hydrocodone, acetaminophen and promethazine. In another embodiment, a composition comprises oxycodone, acetaminophen and promethazine.

Administration

One aspect of the present invention provides a method for preventing an adverse effect such as nausea, vomiting, other gastric upsets, skin rashes, allergic reactions such as swelling, difficulty breathing, closing of throat, abdominal pain, unusual bleeding or bruising and skin rashes in a subject receiving or in need of opioid analgesic therapy by the administration of acetaminophen or other non-opiod analgesic and promethazine or other antihistamine with the chosen opioid analgesics. Accordingly, the invention provides methods for treating pain, comprising administering to a subject in need thereof an effective amount of an opioid analgesic agent, a non-opioid analgesic agent and an agent that reduces side affects of the opioid analgesic agent. In one embodiment, the non-opioid analgesic agent is acetaminophen. In another embodiment, the agent that reduces a adverse effect is promethazine. The administration can continue for only a relatively short time in the case of an acute condition requiring opioid therapy or for long periods in the case of conditions requiring chronic use of opioid analgesics. The dosing of analgesics can be dependent upon the condition being treated, the subject's individual perception of pain and the use of the opioid on a set time schedule as a prophylactic to prevent the onset of pain or on an as needed basis in response to perceived pain. The choice of selecting a dosage of a composition that contains suitable amount of promethazine can be dependent upon the extent and severity of the adverse effects including nausea, vomiting, other gastric upsets, skin rashes, allergic reactions such as swelling, difficulty breathing, closing of throat, abdominal pain, unusual bleeding or bruising and skin rashes in a subject, upon the sensitivity to side-effect-reducing compounds such as promethazine in a subject, upon the likelihood of subject losing medication by vomiting, and/or on an as needed basis in response to perceived adverse effects. The dosage can be assessed by a prescribing professional evaluating the subject, the condition treated, the analgesic to be used, diet and the expected duration of therapy.

In one embodiment, the present invention provides for a method for treating a subject suffering from or susceptible to pain, comprising administering to said subject a pharmaceutical composition comprising an effective amount of a first component which is a non-opioid analgesic, or a pharmaceutically acceptable salt thereof, an effective amount of a second component which is a non-opioid analgesic, or a pharmaceutically acceptable salt thereof and an effective amount of a third component which is an antihistamine.

In another embodiment, a method for treating a subject is provided comprising administering a pharmaceutical composition comprising: an effective amount of a first agent which is a non-opioid analgesic, or a pharmaceutically acceptable salt thereof; an effective amount of a second agent which is an opioid analgesic, or a pharmaceutically acceptable salt thereof; and an effective amount of a third component which is an antihistamine. In one embodiment the at least one adverse effect is selected from the group consisting of nausea, vomiting, other gastric upsets, skin rashes, allergic reactions such as swelling, difficulty breathing, closing of throat, abdominal pain, unusual bleeding or bruising and skin rashes. In one embodiment the non-opioid analgesic is acetaminophen or analogue thereof. In one embodiment, the antihistamine is promethazine. In one embodiment, the opioid analgesic is hydrocodone. In another embodiment the opioid analgesic is oxycodone.

In another embodiment, the present invention provides for a method for preventing a adverse effect such as nausea, vomiting, and a skin rash in a subject receiving or in need of opioid therapy by the administration of acetaminophen or analogue thereof and promethazine with the opioid analgesic. In one embodiment, the opioid analgesic is hydrocodone. In another embodiment the opioid analgesic is oxycodone. In one embodiment, administration of a composition comprising a non-opioid analgesic and an antihistamine enhances the reduction or elimination of adverse effects associated with an opioid analgesic. For example, addition of promethazine and acetaminophen/ibuprofen reduces or eliminates an adverse effect associated with an opioid analgesic in a synergistic manner.

It is believed that administration of a composition of the invention would result in treatment of the subject which includes elimination or reduction of an adverse effect associated with analgesics (e.g., opioids) and enhance the beneficial uses of such analgesics. Such an adverse effect can otherwise render administration of certain analgesics intolerable, due to for example vomiting, nausea, and skin rashes. Therefore, various embodiments of the methods of the invention are directed to target populations of subjects that are susceptible to such an adverse effect(s), thus allowing such subjects to benefit from the pain-alleviating effects of analgesic-based pain relief, administration of which would otherwise be intolerable.

For example, by reducing the risk of vomiting, the risk of subject losing the analgesics (and losing the pain-relieving beneficial effects of analgesics) by vomiting is minimized Furthermore, administration can be adjusted to provide the dose of side-effect-reducing compound to match the subject's analgesic ingestion without separate intervention by the health care professionals. Adding one or more additional active agents, such as promethazine, to the present compositions is believed to result in a composition having reduced potential for abuse and diversion.

Dosage

In various aspects a composition of the invention comprises multiple active agents at the same or different dosages. In some embodiments, the analgesic components may vary in dosages as further described herein, and the antihistamine or antiemetic dosage can be adjusted according to the particular analgesics used.

For example, in various embodiments an opioid analgesic present in a composition of the invention is at a dose of 1.0 mg to about 20 mg, including but not limited to 1.0 mg, 1.5 mg, 2.5 mg, 3.0 mg, 4.0 mg, 5.0 mg, 6.0 mg, 6.5 mg, 7.0 mg, 7.5 mg, 8.0 mg, 8.5 mg, 9.0 mg, 9.5 mg, 10.0, 10.5 mg, 11.0 mg, 12.0 mg, 12.5 mg, 13.0 mg, 13.5 mg, 14.0 mg, 14.5 mg, 15.0 mg, 15.5 mg, 16 mg, 16.5 mg, 17 mg, 17.5 mg, 18 mg, 18.5 mg, 19 mg, 19.5 mg or 20 mg.

In further embodiments for multi-drug compositions of the invention a non-opioid analgesic is present at a doses of 200 mg to about 600 mg, including but not limited to 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg.

In yet further embodiments of the invention, an antiemetic or antihistamine component of a multi-drug composition of the invention is present at a dose of 0.5 mg to about 60 mg of promethazine, including but not limited to 0.5 mg, 1.0 mg, 1.5 mg, 2.0 mg, 2.5 mg, 3.0 mg, 3.5 mg, 4.0 mg, 4.5 mg, 5.0 mg, 5.5 mg, 6.0 mg, 6.5 mg, 7.0 mg, 7.5 mg, 8.0 mg, 8.5 mg, 9,0 mg, 9.5 mg, 10 mg, 10.5 mg, 11 mg, 11.5 mg, 12.0 mg, 12.5 mg, 13.0 mg, 13.5 mg, 14.0 mg, 14.5 mg, 15.0 mg, 15.5 mg, 16 mg, 16.5 mg, 17 mg, 17.5 mg, 18 mg, 18.5 mg, 19 mg, 19.5 mg or 20 mg, 25 mg, 30 mg, 35 mg, 40 mg, 45 mg, 50 mg, 55 mg or 60 mg.

In one embodiment, a composition of the invention comprises hydrocodone, a pharmaceutically acceptable salt or its thiosemicarbazone, p-nitrophenylhydrazone, o-methyloxime, semicarbazone, or bis(methylcarbamate) (each of the foregoing being a hydrocodone agent or derivative); acetaminophen; and promethazine. Furthermore, the hydrocodone agent is present in a range of about 1.0 mg to about 20 mg, including but not limited to 1.0 mg, 1.5 mg, 2.5 mg, 3.0 mg, 4.0 mg, 5.0 mg, 6.0 mg, 6.5 mg, 7.0 mg, 7.5 mg, 8.0 mg, 8.5 mg, 9.0 mg, 9.5 mg, 10.0, 10.5 mg, 11.0 mg, 12.0 mg, 12.5 mg, 13.0 mg, 13.5 mg, 14.0 mg, 14.5 mg, 15.0 mg, 15.5 mg, 16 mg, 16.5 mg, 17 mg, 17.5 mg, 18 mg, 18.5 mg, 19 mg, 19.5 mg or 20 mg. Furthermore, the acetaminophen is in a range of about 200 mg to about 600 mg, including but not limited to 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg. In addition, the promethazine is between about 0.5 mg to about 60 mg, including but not limited to 0.5 mg, 1.0 mg, 1.5 mg, 2.0 mg, 2.5 mg, 3.0 mg, 3.5 mg, 4.0 mg, 4.5 mg, 5.0 mg, 5.5 mg, 6.0 mg, 6.5 mg, 7.0 mg, 7.5 mg, 8.0 mg, 8.5 mg, 9,0 mg, 9.5 mg, 10 mg, 10.5 mg, 11 mg, 11.5 mg, 12.0 mg, 12.5 mg, 13.0 mg, 13.5 mg, 14.0 mg, 14.5 mg, 15.0 mg, 15.5 mg, 16 mg, 16.5 mg, 17 mg, 17.5 mg, 18 mg, 18.5 mg, 19 mg, 19.5 mg or 20 mg, 25 mg, 30 mg, 35 mg, 40 mg, 45 mg, 50 mg, 55 mg or 60 mg.

In various embodiments, a composition of the invention comprises hydrocodone, acetaminophen and promethazine, wherein the composition comprises the respective agents in a ratio of about (1 to 2): (40 to 45):(1 to 2), such as about 1:40:1, 1:40:1.1, 1:40:1.2, 1:40:1.3, 1:40:1.4, 1:40:1.5, 1:40:1.6, 1:40:1.7, 1:40:1.8, 1:40:1.9, 1:40:2, 1.1:40:1, 1.2:40:1, 1.3:40:1, 1.4:40:1, 1.5:40:1, 1.6:40:1, 1.7:40:1, 1.8:40:1, 1.9:40:1, 2:40:1, 1:41:1, 1:41:1.1, 1:41:1.2, 1:41:1.3, 1:41:1.4, 1:41:1.5, 1:41:1.6, 1:41:1.7, 1:41:1.8, 1:41:1.9, 1:41:2, 1.1:41:1, 1.2:41:1, 1.3:41:1, 1.4:41:1, 1.5:41:1, 1.6:41:1, 1.7:41:1, 1.8:41:1, 1.9:41:1, 2:41:1, 1:42:1, 1:42:1.1, 1:42:1.2, 1:42:1.3, 1:42:1.4, 1:42:1.5, 1:42:1.6, 1:42:1.7, 1:42:1.8, 1:42:1.9, 1:42:2, 1.1:42:1, 1.2:42:1, 1.3:42:1, 1.4:42:1, 1.5:42:1, 1.6:42:1, 1.7:42:1, 1.8:42:1, 1.9:42:1, 2:42:1, 1:43:1, 1:43:1.1, 1:43:1.2, 1:43:1.3, 1:43:1.4, 1:43:1.5, 1:43:1.6, 1:43:1.7, 1:43:1.8, 1:43:1.9, 1:43:2, 1.1:43:1, 1.2:43:1, 1.3:43:1, 1.4:43:1, 1.5:43:1, 1.6:43:1, 1.7:43:1, 1.8:43:1, 1.9:43:1, 2:43:1, 1:43.1:1, 1:43.1:1.1, 1:43.1:1.2, 1:43.1:1.3, 1:43.1:1.4, 1:43.1:1.5, 1:43.1:1.6, 1:43.1:1.7, 1:43.1:1.8, 1:43.1:1.9, 1:43.1:2, 1.1:43.1:1, 1.2:43.1:1, 1.3:43.1:1, 1.4:43.1:1, 1.5:43.1:1, 1.6:43.1:1, 1.7:43.1:1, 1.8:43.1:1, 1.9:43.1:1, 2:43.1:1, 1:43.2:1, 1:43.2:1.1, 1:43.2:1.2, 1:43.2:1.3, 1:43.2:1.4, 1:43.2:1.5, 1:43.2:1.6, 1:43.2:1.7, 1:43.2:1.8, 1:43.2:1.9, 1:43.2:2, 1.1:43.2:1, 1.2:43.2:1, 1.3:43.2:1, 1.4:43.2:1, 1.5:43.2:1, 1.6:43.2:1, 1.7:43.2:1, 1.8:43.2:1, 1.9:43.2:1, 2:43.2:1, 1:43.3:1, 1:43.3:1.1, 1:43.3:1.2, 1:43.3:1.3, 1:43.3:1.4, 1:43.3:1.5, 1:43.3:1.6, 1:43.3:1.7, 1:43.3:1.8, 1:43.3:1.9, 1:43.3:2, 1.1:43.3:1, 1.2:43.3:1, 1.3:43.3:1, 1.4:43.3:1, 1.5:43.3:1, 1.6:43.3:1, 1.7:43.3:1, 1.8:43.3:1, 1.9:43.3:1, 2:43.3:1, 1:43.4:1, 1:43.4:1.1, 1:43.4:1.2, 1:43.4:1.3, 1:43.4:1.4, 1:43.4:1.5, 1:43.4:1.6, 1:43.4:1.7, 1:43.4:1.8, 1:43.4:1.9, 1:43.4:2, 1.1:43.4:1, 1.2:43.4:1, 1.3:43.4:1, 1.4:43.4:1, 1.5:43.4:1, 1.6:43.4:1, 1.7:43.4:1, 1.8:43.4:1, 1.9:43.4:1, 2:43.4:1, 1:43.5:1, 1:43.5:1.1, 1:43.5:1.2, 1:43.5:1.3, 1:43.5:1.4, 1:43.5:1.5, 1:43.5:1.6, 1:43.5:1.7, 1:43.5:1.8, 1:43.5:1.9, 1:43.5:2, 1.1:43.5:1, 1.2:43.5:1, 1.3:43.5:1, 1.4:43.5:1, 1.5:43.5:1, 1.6:43.5:1, 1.7:43.5:1, 1.8:43.5:1, 1.9:43.5:1, 2:43.5:1, 1:43.6:1, 1:43.6:1.1, 1:43.6:1.2, 1:43.6:1.3, 1:43.6:1.4, 1:43.6:1.5, 1:43.6:1.6, 1:43.6:1.7, 1:43.6:1.8, 1:43.6:1.9, 1:43.6:2, 1.1:43.6:1, 1.2:43.6:1, 1.3:43.6:1, 1.4:43.6:1, 1.5:43.6:1, 1.6:43.6:1, 1.7:43.6:1, 1.8:43.6:1, 1.9:43.6:1, 2:43.6:1, 1:43.7:1, 1:43.7:1.1, 1:43.7:1.2, 1:43.7:1.3, 1:43.7:1.4, 1:43.7:1.5, 1:43.7:1.6, 1:43.7:1.7, 1:43.7:1.8, 1:43.7:1.9, 1:43.7:2, 1.1:43.7:1, 1.2:43.7:1, 1.3:43.7:1, 1.4:43.7:1, 1.5:43.7:1, 1.6:43.7:1, 1.7:43.7:1, 1.8:43.7:1, 1.9:43.7:1, 2:43.7:1, 1:43.8:1, 1:43.8:1.1, 1:43.8:1.2, 1:43.8:1.3, 1:43.8:1.4, 1:43.8:1.5, 1:43.8:1.6, 1:43.8:1.7, 1:43.8:1.8, 1:43.8:1.9, 1:43.8:2, 1.1:43.8:1, 1.2:43.8:1, 1.3:43.8:1, 1.4:43.8:1, 1.5:43.8:1, 1.6:43.8:1, 1.7:43.8:1, 1.8:43.8:1, 1.9:43.8:1, 2:43.8:1, 1:43.9:1, 1:43.9:1.1, 1:43.9:1.2, 1:43.9:1.3, 1:43.9:1.4, 1:43.9:1.5, 1:43.9:1.6, 1:43.9:1.7, 1:43.9:1.8, 1:43.9:1.9, 1:43.9:2, 1.1:43.9:1, 1.2:43.9:1, 1.3:43.9:1, 1.4:43.9:1, 1.5:43.9:1, 1.6:43.9:1, 1.7:43.9:1, 1.8:43.9:1, 1.9:43.9:1, 2:43.9:1, 1:44:1, 1:44:1.1, 1:44:1.2, 1:44:1.3, 1:44:1.4, 1:44:1.5, 1:44:1.6, 1:44:1.7, 1:44:1.8, 1:44:1.9, 1:44:2, 1.1:44:1, 1.2:44:1, 1.3:44:1, 1.4:44:1, 1.5:44:1, 1.6:44:1, 1.7:44:1, 1.8:44:1, 1.9:44:1, 2:44:1, 1:45:1, 1:45:1.1, 1:45:1.2, 1:45:1.3, 1:45:1.4, 1:45:1.5, 1:45:1.6, 1:45:1.7, 1:45:1.8, 1:45:1.9, 1:45:2, 1.1:45:1, 1.2:45:1, 1.3:45:1, 1.4:45:1, 1.5:45:1, 1.6:45:1, 1.7:45:1, 1.8:45:1, 1.9:45:1, or 2:45:1. For example, in one embodiment, the ratio of amounts for each active agent is (1): (43.33):(1.67) for hydrocodone, acetaminophen and promethazine, respectively.

In another embodiment, the pharmaceutical composition comprises oxycodone, a pharmaceutically acceptable salt or its thiosemicarbazone, p-nitrophenylhydrazone, o-methyloxime, semicarbazone, or bis(methylcarbamate) (each of the foregoing being a hydrocodone agent or derivative); acetaminophen; and promethazine. Furthermore the oxycodone agent is present in a range of about 1 mg to about 200 mg, including but not limited to 1.0 mg, 1.5 mg, 2.5 mg, 3.0 mg, 4.0 mg, 4.5 mg, 5.0 mg, 5.5 mg, 6.0 mg, 6.5 mg, 7.0 mg, 7.5 mg, 8.0 mg, 8.5 mg, 9.0 mg, 9.5 mg, 10.0, 10.5 mg, 11.0 mg, 12.0 mg, 12.5 mg, 13.0 mg, 13.5 mg, 14.0 mg, 14.5 mg, 15.0 mg, 15.5 mg, 16 mg, 16.5 mg, 17 mg, 17.5 mg, 18 mg, 18.5 mg, 19 mg, 19.5 mg or 20 mg, 30 mg, 40 mg, 50 mg, 70 mg, 100 mg, 130 mg, 160, 190 mg, 200 mg. Furthermore, the acetaminophen is in a range of between about 200 mg to about 600 mg, including but not limited to 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, and a preferred range of about 325 mg. The pharmaceutical composition further comprises between about 0.5 mg to about 60 mg of an antihistamine (e.g., promethazine), including but not limited to 0.5 mg, 1.0 mg, 1.5 mg, 2.0 mg, 2.5 mg, 3.0 mg, 3.5 mg, 4.0 mg, 4.5 mg, 5.0 mg, 5.5 mg, 6.0 mg, 6.5 mg, 7.0 mg, 7.5 mg, 8.0 mg, 8.5 mg, 9,0 mg, 9.5 mg, 10 mg, 10.5 mg, 11.0 mg, 11.5 mg, 12.0 mg, 12.5 mg, 15 mg, 20 mg, 30 mg, 40 mg, 50 mg, or 60 mg.

In one embodiment, the pharmaceutical composition provides promethazine at 12.5 mg. In one embodiment, a composition of the invention comprises oxycodone, acetaminophen and promethazine, wherein the composition comprises the agents in a ratio of about (1 to 2): (40 to 45):(1 to 2), respectively. For example, in one embodiment, the ratio of amounts for each active agent is (1): (43.33):(1.67) for oxycodone, acetaminophen and promethazine, respectively. In one embodiment, a pharmaceutical composition of the invention comprises an antihistamine (e.g., promethazine) at a lower dosage than that which the antihistamine is administered alone. For example, the antihistamine is provided in the composition at a dosage to prevent sedation, which may be observed with relatively higher dosages of promethazine. Thus in some embodiments, promethazine is provided at 1, 2, 3, 4, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 33, 33.5, 34, 34.5, 35, 36, 36.5, 37, 37.5, 38, 38.5, 39, 39.5, 40, 40.5, 41, 41.5, 42, 42.5, 43, 43.5, 44, 44.5, 45, 45.5, 46, 46.5, 47, 47.5, 48, 48.5, 49, 49.5 or 50. Therefore, an antihistamine or antiemetic (e.g., promethazine) can be provided at a dosage that is effective in reducing adverse affects associated with the opioid analgesic and/or non-opioid analgesic, but is at a relative low enough dosage (e.g., given the subject's weight) to prevent sedation associated with the antihistamine/antiemetic. Examples of adverse effects include acute liver toxicity, allergic reactions such as swelling, difficulty breathing, closing of throat, abdominal pain, nausea, unusual bleeding or bruising.

In one embodiment, a pharmaceutical composition of the invention comprises 6-8 mg of hydrocodone (such as about 6.0 mg, 6.1 mg, 6.2 mg, 6.3 mg, 6.4 mg, 6.5 mg, 6.6 mg, 6.7 mg, 6.8 mg, 6.9 mg, 7.0 mg, 7.1 mg, 7.2 mg, 7.3 mg, 7.4 mg, 7.5 mg, 7.6 mg, 7.7 mg, 7.8 mg, 7.9 mg, or 8.0 mg,), 310-330 mg of acetaminophen (such as about 310 mg, 315 mg, 320 mg, or 325 mg), and 5-13 mg of promethazine (such as about 10 mg, 10.5 mg, 11.0 mg, 11.5 mg, 12.0 mg, 12.5 mg, 13.0, mg, 13.5 mg, 14.0 mg, 14.5 mg, or 15 mg). The hydrocodone and the acetaminophen can be formulated using conventional technologies to provide for an extended time release over a desired dosage interval. All or some of the promethazine is formulated for immediate release to help abate common adverse effects associated with the hydrocodone and/or acetaminophen including nausea, vomiting, other gastric upsets, skin rashes, allergic reactions such as swelling, difficulty breathing, closing of throat, abdominal pain, unusual bleeding or bruising.

In one embodiment, a composition of the invention comprises from 1% to 20% by weight of an antihistamine (such as 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, or 20%); from 10% to 80% by weight a non-opioid analgesic (such as 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, 20%, 20.5%, 21%, 21.5%, 22%, 22.5%, 23%, 23.5%, 24%, 24.5%, 25%, 25.5%, 26%, 26.5%, 27%, 27.5%, 28%, 28.5%, 29%, 29.5%, 30%, 30.5%, 31%, 31.5%, 32%, 32.5%, 33%, 33.5%, 34%, 34.5%, 35%, 35.5%, 36%, 36.5%, 37%, 37.5%, 38%, 38.5%, 39%, 39.5%, 40%, 40.5%, 41%, 41.5%, 42%, 42.5%, 43%, 43.5%, 44%, 44.5%, 45%, 45.5%, 46%, 46.5%, 47%, 47.5%, 48%, 48.5%, 49%, 49.5%, 50%, 50.5%, 51%, 51.5%, 52%, 52.5%, 53%, 53.5%, 54%, 54.5%, 55%, 55.5%, 56%, 56.5%, 57%, 57.5%, 58%, 58.5%, 59%, 59.5%, 60%, 60.5%, 61%, 61.5%, 62%, 62.5%, 63%, 63.5%, 64%, 64.5%, 65%, 65.5%, 66%, 66.5%, 67%, 67.5%, 68%, 68.5%, 69%, 69.5%, 70%, 70.5%, 71%, 71.5%, 72%, 72.5%, 73%, 73.5%, 74%, 74.5%, 75%, 75.5%, 76%, 76.5%, 77%, 77.5%, 78%, 78.5%, 79%, 79.5%, 80%); and from 1% to 20% by weight of an opioid analgesic (such as 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, or 20%).

In one embodiment, a composition of the invention comprises 6-8 mg of oxycodone HCl (such as about 7.5 mg), 310-330 mg of acetaminophen (such as about 325 mg), and 6-8 mg of promethazine (such as about 12.5 mg). The oxycodone HCl and the acetaminophen can be formulated using conventional technologies to provide for an extended time release over a desired dosage interval. All or some of the promethazine is formulated for immediate release. Therefore, in one embodiment, administration of a composition of the invention comprising such a promethazine active agent can result in reduced, abated or eliminated adverse effects associated with the oxycodone HCl and/or acetaminophen. Reduced, abated or eliminated adverse effects include but are not limited to including nausea, vomiting, other gastric upsets, skin rashes, allergic reactions such as swelling, difficulty breathing, closing of throat, abdominal pain, unusual bleeding or bruising or any combination thereof.

The dosages and concentrations of active agents in the compositions may be varied as desired, as further described herein. Depending on the subject and/or condition being treated and on the administration route, the active agent in a composition can generally be administered in dosages of 0.01 mg to 500 mg V/kg body weight per day, e.g. about 20 mg/day for an average person. The dosage can be adjusted based on the mode of administration. A typical dosage may be one administration daily, or multiple administrations daily.

Of course for prolonged or controlled-release dosage forms (e.g., patches) the unit dose is designed for administration over a defined period of time. In some embodiments, dosage for one or a combination of agents can be from 0.01 to 5 mg, 1 to 10 mg, 5 to 20 mg, 10 to 50 mg, 20 to 100 mg, 50 to 150 mg, 100 to 250 mg, 150 to 300 mg, 250 to 500 mg, 300 to 600 mg or 500 to 1000 mg V/kg body weight. Dose levels can vary as a function of the specific compound, the severity of the symptoms and the susceptibility of the subject to adverse effects.

Routes of Administration

In various embodiments of the present invention, the active agents are formulated to be administered through oral dosage forms (e.g., tablets, capsules, gels), inhalations, nasal sprays, patches, absorbing gels, liquids, liquid tannates, suppositories, injections, I.V. drips, other delivery methods, or a combination thereof to treat subjects. Administration may be performed in a variety of ways, including, but not limited to orally, subcutaneously, intravenously, intranasally, intraotically, transdermally, topically (e.g., gels, salves, lotions, creams, etc.), intraperitoneally, intramuscularly, intrapulmonary (e.g., AERx® inhalable technology commercially available from Aradigm, or Inhance, pulmonary delivery system commercially available from Inhale Therapeutics), vaginally, parenterally, rectally, or intraocularly.

To prepare the present compositions, the active agents can be mixed with a suitable pharmaceutically acceptable carrier. Upon mixing of the compounds, the resulting composition can be a solid, a half-solid, a solution, suspension, or an emulsion. Such compositions can be prepared according to methods known to those skilled in the art. The forms of the resulting compositions can depend upon a variety of factors, including the intended mode of administration and the solubility of the compounds in the selected carrier or vehicle. The effective concentration of analgesics is sufficient for lessening or alleviating pain. In one embodiment of the invention, the components of the present compositions are at least one opioid analgesic agent (e.g., hydrocodone/oxycodone), one non-opioid analgesic agent (e.g., acetaminophen), and one antihistamine agent (e.g., promethazine). In other embodiments, administration comprises administration of an antihistamine (e.g., promethazine) separately, prior to, or during administration of the analgesic formulations described herein (e.g., which comprises hydrocodone and acetaminophen).

The agents of the compositions and methods of the present invention can be administered by the nasal inhalation route using conventional nebulizers or by oxygen aerosolization to provide convenient pain relief with reduced adverse effects. The agents can be suspended or dissolved in a pharmacologically acceptable inhalation carrier. Examples of such carriers are distilled water, water/ethanol mixtures, and physiological saline solution. Conventional additives including sodium chloride, glucose, citric acid and the like may be employed in these dosage forms to stabilize or to provide isotonic media. In one embodiment of the invention, the compositions suitable for nasal inhalation by oxygen aerosolization administration comprise hydrocodone or oxycodone, acetaminophen, and promethazine. In other embodiments, an antihistamine (e.g., promethazine) can be administered separately, prior to, or during administration of the compositions described herein (e.g., those comprising hydrocodone and acetaminophen).

The agents of the present invention can also be administered as a self-propelled dosage unit in aerosol form suitable for inhalation therapy. Suitable means for employing the aerosol inhalation therapy technique are described, for example, in U.S. Pat. No. 6,913,768 to Couch et al., incorporated herein by reference in its entirety. The agent can be suspended in an inert propellant such as a mixture of dichlorodifluoromethane and dichlorotetrafluoroethane, together with a co-solvent such as ethanol, together with other medications such as albuterol, together with flavoring materials and stabilizers. In one embodiment of the invention, the agents useful for a self-propelled dosage unit in aerosol form administration are hydrocodone or oxycodone, acetaminophen, and promethazine.

The agents of the compositions and methods of the present invention can also be administered as nasal spray/drop compositions, which can conveniently and safely be applied to subjects to effectively treat pain with reduced adverse effects. The compositions may further comprise a water soluble polymer such as polyvinylpyrrolidone, together with other medications such as sumatriptan, together with bioadhesive material. In one embodiment of the invention, the components of a composition for nasal spray or drop administration are hydrocodone or oxycodone agent, acetaminophen, and promethazine.

The compositions of the present invention can also be administered topically to the skin of a subject. The agents can be mixed with a pharmaceutically acceptable carrier or a base which is suitable for topical application to skin to form a dermatological composition. Suitable examples of carrier or base include, but not limited to, water, glycols, alcohols, lotions, creams, gels, emulsions, and sprays. A dermatological composition comprising an analgesic agent can be integrated into a topical dressing, medicated tape, dermal patch absorbing gel and cleansing tissues. In one embodiment of the invention, the dermatological composition comprises hydrocodone or oxycodone, acetaminophen, and promethazine.

The compositions of the present invention can also be in liquid or liquid tannate form.

The liquid formulations can comprise, for example, an agent in water-in-solution and/or suspension form; and a vehicle comprising polyethoxylated castor oil, alcohol and/or a polyoxyethylated sorbitan mono-oleate with or without flavoring. Each dosage form comprises an effective amount of an active agent and can optionally comprise pharmaceutically inert agents, such as conventional excipients, vehicles, fillers, binders, disentegrants, solvents, solubilizing agents, sweeteners, coloring agents and any other inactive agents that can be included in pharmaceutical dosage forms for oral administration. Examples of such vehicles and additives can be found in Remington's Pharmaceutical Sciences, 17th edition (1985). Therefore, in one embodiment a liquid composition of the invention comprises an opioid analgesic (e.g., hydrocodone or oxycodone), a non-opioid analgesic (e.g., acetaminophen) and an antihistamine (e.g., promethazine).

The compositions of the present invention can also be administered in a suppository form, comprising an outer layer containing the composition in a suppository base. The suppository base may, for example, be any conventional suppository base material such as glycogelatin, polyethylene glycol, fractionated palm kernel oil, or one or more natural, synthetic or semisynthetic hard fats such as cocoa butter. Therefore, in one embodiment of the invention, the base material is mixed with an opioid analgesic (e.g., hydrocodone/oxycodone), a non-opioid analgesic (e.g., acetaminophen) and an antihistamine (e.g., promethazine).

The compositions of the present invention can also be administered in injection-ready stable liquids for injection or I.V. drip. For example, saline or other injection-ready liquid can be mixed with an opioid analgesic (e.g., hydrocodone or oxycodone), a non-opioid analgesic (e.g., acetaminophen) and an antihistamine (e.g., promethazine).

Dosage Forms

In various embodiments of the invention, a composition is in one or more dosage form. For example, a composition can be administered in a solid or liquid form. Examples of solid dosage forms include but are not limited to discrete units in capsules or tablets, as a powder or granule, or present in a tablet conventionally formed by compression molding. Such compressed tablets may be prepared by compressing in a suitable machine the three or more agents and a pharmaceutically acceptable carrier. The molded tablets can be optionally coated or scored, having indicia inscribed thereon and can be so formulated as to cause immediate, substantially immediate, slow, or controlled release of the hydrocodone and/or the acetaminophen. Furthermore, dosage forms of the invention can comprise acceptable carriers or salts known in the art, such as those described in the Handbook of Pharmaceutical Excipients, American Pharmaceutical Association (1986), incorporated by reference herein.

In one embodiment, the components are mixed with a pharmaceutical excipient to form a solid preformulation composition comprising a homogeneous mixture of compounds of the present invention. When referring to these compositions as "homogeneous", it is meant that the agents are dispersed evenly throughout the composition so that the composition can be subdivided into unit dosage forms such as tablets or capsules. This solid preformulation composition can then subdivided into unit dosage forms of the type described above comprising from, for example, about 1.0 mg to about 15 mg of an opioid, such as hydrocodone or oxycodone of the present invention.

The compositions can be formulated, in the case of capsules or tablets, to be swallowed whole, for example with water. The inclusion of the side-effect-reducing agent such as an antihistamine or antiemetic to abate common symptoms of nausea and vomiting are believed beneficial in that promethazine or the like will eliminate or minimize the amount of discomfort. Adverse effects reduced or eliminated include but are not limited to nausea, vomiting, other gastric upsets, skin rashes, allergic reactions such as swelling, difficulty breathing, closing of throat, abdominal pain, unusual bleeding or bruising Frequently, subjects taking opioids have adverse effects including vomiting that can occur shortly after taking a first or subsequent dose. As a consequence, a portion of the opioid dose is subsequently lost, making it difficult to accurately gauge replacement dosages for the subject, and for subjects outside of a hospital or clinic environment, there might not be any alternative form of pain medication readily available. As a consequence, subjects experiencing gastric discomfort such as vomiting will lack the beneficial effects of the opioid analgesic and experience the additional discomfort and enhanced pain associated with vomiting. This problem is solved by also administering promethazine, which reduces side-effects.

The dosage forms of the present invention can be manufactured using processes that are well known to those of skill in the art. For example, for the manufacture of bi-layered tablets, the agents can be dispersed uniformly in one or more excipients, for example, using high shear granulation, low shear granulation, fluid bed granulation, or by blending for direct compression. Excipients include diluents, binders, disintegrants, dispersants, lubricants, glidants, stabilizers, surfactants and colorants. Diluents, also termed "fillers", can be used to increase the bulk of a tablet so that a practical size is provided for compression. Non-limiting examples of diluents include lactose, cellulose, microcrystalline cellulose, mannitol, dry starch, hydrolyzed starches, powdered sugar, talc, sodium chloride, silicon dioxide, titanium oxide, dicalcium phosphate dihydrate, calcium sulfate, calcium carbonate, alumina and kaolin. Binders can impart cohesive qualities to a tablet formulation and can be used to help a tablet remain intact after compression. Non-limiting examples of suitable binders include starch (including corn starch and pregelatinized starch), gelatin, sugars (e.g., glucose, dextrose, sucrose, lactose and sorbitol), celluloses, polyethylene glycol, waxes, natural and synthetic gums, e.g., acacia, tragacanth, sodium alginate, and synthetic polymers such as polymethacrylates and polyvinylpyrrolidone. Lubricants can also facilitate tablet manufacture; non-limiting examples thereof include magnesium stearate, calcium stearate, stearic acid, glyceryl behenate, and polyethylene glycol. Disintegrants can facilitate tablet disintegration after administration, and non-limiting examples thereof include starches, alginic acid, crosslinked polymers such as, e.g., crosslinked polyvinylpyrrolidone, croscarmellose sodium, potassium or sodium starch glycolate, clays, celluloses, starches, gums and the like. Non-limiting examples of suitable glidants include silicon dioxide, talc and the like. Stabilizers can inhibit or retard drug decomposition reactions, including oxidative reactions. Surfactants can also included and can be anionic, cationic, amphoteric or nonionic. If desired, the tablets can also comprise nontoxic auxiliary substances such as pH buffering agents, preservatives, e.g., antioxidants, wetting or emulsifying agents, solubilizing agents, coating agents, flavoring agents, and the like.

Extended or controlled-release formulations can comprise one or more combination of excipients that slow the release of the agents by coating or temporarily bonding or decreasing their solubility of the active agents. Examples of these excipients include cellulose ethers such as hydroxypropylmethylcellulose (e.g., Methocel K4M), polyvinylacetate-based excipients such as, e.g., Kollidon SR, and polymers and copolymers based on methacrylates and methacrylic acid such as, e.g., Eudragit NE 30D. In one embodiment of the invention, the analgesic agents (e.g., hydrocodone or oxycodone, and acetaminophen) are formulated for extended or controlled-release while the promethazine is formulated for immediate release. In another embodiment, all agents are formulated for extended or controlled-release.

Pharmaceutical carriers or vehicles suitable for administration of the compounds provided herein include all such carriers known to those skilled in the art to be suitable for the particular mode of administration. In addition, the analgesics and promethazine can also be administered with other components that do not impair the desired action, or with components that supplement the desired action, or have another action. As noted above, a composition can comprise additional (e.g., a fourth, fifth, sixth, etc.) addition active compounds.

In one embodiment of the present invention, the composition comprises three or more active agents wherein at least one active agent is in immediate release form. In this embodiment the immediate-release form is included in an amount that is effective to shorten the time to its maximum concentration in the blood. By way of example, certain immediate-release pharmaceutical preparations are taught in United States Patent Publication US 2005/0147710A1 entitled, "Powder Compaction and Enrobing" which is incorporated herein in its entirety by reference.

In a further embodiment of the present invention, the component in immediate-release form is a component that reduces abates or eliminates and/or suppresses a adverse effect associated with one or more opioid analgesics.

For example, the immediate-release active can be an antihistamine or antiemetic, which reduces, abates or eliminates an adverse effect associated with opioid and/or non-opioid analgesics described herein. Thus, in one embodiment, of the invention, the analgesic formulation comprises an opioid and non-opioid analgesic (e.g., hydrocodone or oxycodone and acetaminophen, respectively) and an antihistamine (e.g., promethazine).

In a further embodiment of the present invention, all or less than all of the total amount of the antiemetic or antihistamine agent is formulated in immediate-release form, as described herein.

A variety of known methods and materials may be used to bring about the immediate release. For instance, placement of the agent along an exterior of a tablet (e.g., coating the exterior or formulating the outer layer with the agent) and/or combined with forming a tablet by compressing the powder using low compaction can produce immediate-release of the agent from the composition.

In a specific embodiment, an effective amount of the promethazine in immediate-release form may be coated onto a substrate. For example, where the extended release of one or more analgesics from a formulation is due to a controlled-release coating, an immediate-release layer comprising promethazine can overcoat the controlled-release coating. On the other hand, the immediate-release layer of promethazine can be coated onto the surface of a substrate wherein hydrocodone and/or oxycodone is incorporated in a controlled release matrix. Where a plurality of controlled-release substrates comprising an effective unit dose of an analgesic (e.g., multiparticulate systems including pellets, spheres, beads and the like) are incorporated into a hard gelatin capsule, the side-effect-reducing compound can be incorporated into the gelatin capsule via inclusion of an amount of immediate-release promethazine as a powder or granulate within the capsule. Alternatively, the gelatin capsule itself can be coated with an immediate-release layer of promethazine. One skilled in the art recognizes still other alternative means of incorporating the immediate release side-effect-reducing compound into the unit dose. By including an effective amount of immediate-release side-effect-reducing compound such as promethazine in the unit dose, the experience of adverse effects including nausea, vomiting, other gastric upsets, skin rashes, allergic reactions such as swelling, difficulty breathing, closing of throat, abdominal pain, unusual bleeding or bruising and skin rashes in subjects can be significantly reduced.

In one embodiment of the present invention, the composition comprises three or more active agents wherein at least one active agent is in controlled-release form. The controlled-release form can be in an amount that is effective to protect the agent from rapid elimination from the body. Certain preparations relating to the controlled release of a pharmaceutical are taught in United States Patent Publication US 2005/0147710A1 entitled, "Powder Compaction and Enrobing" which is incorporated herein in its entirety by reference.

In a further embodiment of the present invention, the agent in controlled-release form is an opioid analgesics such as, for example, hydrocodone, or oxycodone. In one embodiment of the invention, compositions comprise one or more carriers that protect the agents against rapid elimination from the body, such as time-release formulations or coatings. Such carriers include controlled-release formulations, including, for example, microencapsulated delivery systems. The active agents can be included in the pharmaceutically acceptable carrier in amounts sufficient to treat a subject's pain, with reduced adverse effects.

In certain embodiments the compositions are in oral-dosage form and comprise a matrix that includes, for example, a controlled-release material and an analgesic such as hydrocodone or a pharmaceutically acceptable salt thereof. In certain embodiments, the matrix is compressible into a tablet and can be optionally overcoated with a coating that can control the release of the analgesics including hydrocodone or pharmaceutically acceptable salt thereof from the composition. In this embodiment blood levels of analgesics are maintained within a therapeutic range over an extended period of time. In to certain alternate embodiments, the matrix is encapsulated.

Tablets or capsules containing a composition of the present invention can be coated or otherwise compounded to provide a dosage form affording the advantage of prolonged action. For example, the tablet or capsule can contain an inner dosage and an outer dosage component, the latter being in the form of an envelope over the former. The two components can be separated by an enteric layer that serves to resist disintegration in the stomach and permit the inner component to pass intact into the duodenum or to be delayed in release. For controlled extended release, the capsule can also have micro drilled holes.

A coating comprising a side-effect-reducing compound such as promethazine, in immediate release form, can be added to the outside of a controlled-release tablet core to produce a final dosage form. Such a coating can be prepared by admixing a compound like promethazine with polyvinylpyrrolidone (PVP) 29/32 or hydroxypropyl methylcellulose (HPMC) and water/isopropyl alcohol and triethyl acetate. Such an immediate-release coating can be spray coated onto the tablet cores. The immediate-release coating can also be applied using a press-coating process with a blend consisting of 80% by weight promethazine and 20% by weight of lactose and hydroxypropyl methylcellulose type 2910. Press-coating techniques are known in the art and are described in U.S. Pat. No. 6,372,254 to Ting et al., incorporated herein by reference in its entirety.

The immediate-release or controlled-release dosage forms of the present invention can also take the form of a bi-layered tablet, which comprises a first layer and a second layer. The first layer comprises a first drug selected from analgesics, antitussives, antihistamines, antiemetics. The second layer comprises a second drug selected from analgesics, antitussives, antihistamines, antiemetics. The second drug is the same as or different from the first drug. The bi-layered tablet can provide a plasma concentration within the therapeutic range of the second drug over a period which is coextensive with at least about 70% of the period (e.g., 12 hours) within which the bi-layered tablet provides a plasma concentration within the therapeutic range of the first drug.

In a further aspect of the bi-layered tablet, the first layer is an immediate release layer and/or the second layer is a controlled-release layer.

In one aspect of the bi-layered tablet of the present invention, both layers can comprise an opioid analgesic such as hydrocodone or oxycodone; a non-opioid analgesic such as acetaminophen; and a compound, such as promethazine, to reduce or suppress adverse effects.

In a further aspect of the bi-layered tablet of the present invention, the first layer comprises promethazine and the second layer comprises hydrocodone or oxycodone. The first or second layer can further comprise acetaminophen.

In one embodiment of the present invention, the components are released from a multi-layered tablet that comprises a first layer and a second layer. In this embodiment the first layer comprises a first drug which is selected from analgesics, antitussives, antihistamines, antiemetics. The second layer comprises a second drug which is selected from analgesics, antitussives, antihistamines, antiemetics. The second drug can be the same as or different from the first drug. In one aspect of the multi-layered tablet, the second drug can have a plasma half-life that differs from the plasma half-life of the first drug by at least about 2 hours.

In a further aspect of the multi-layered tablet, the first layer is an immediate-release layer and/or the second layer is a controlled release layer.

In one embodiment of the multi-layered tablet of the present invention, both the first layer and the second layer can comprise an opioid analgesic such as hydrocodone or oxycodone; a non-opioid analgesic such as acetaminophen; and compound to reduce or suppress adverse effects such as promethazine.

In a further embodiment of the multi-layered tablet of the present invention, the first layer comprises promethazine and the second layer comprises hydrocodone or oxycodone. The first or second layer can further comprise acetaminophen.

The immediate-release or controlled release dosage forms of the present invention can also take the form of pharmaceutical particles manufactured by a variety of methods, including but not limited to high-pressure homogenization, wet or dry ball milling, or small particle precipitation (nGimat's NanoSpray$^{SM}$). Other methods to make a suitable powder formulation are the preparation of a solution of active ingredients and excipients, followed by precipitation, filtration, and pulverization, or followed by removal of the solvent by freeze-drying, followed by pulverization of the powder to the desired particle size. In one embodiment the pharmaceutical particles are manufactured to a final size of 3-1000 uM, such as at most 3, 4, 5, 6, 7, 8, 9,10, 20, 30, 40, 50, 60, 70, 80, 90, 100, 150, 200, 250, 300, 350, 400, 450, 500, 550, 600, 650, 700, 750, 800, 850, 900, 950, 1000 uM. In another embodiment the pharmaceutical particles are manufactured to a final size of 10-500 uM. embodiment the pharmaceutical particles are manufactured to a final size of 50-600 uM. embodiment the pharmaceutical particles are manufactured to a final size of 100-800 uM. These dosage forms can include immediate-release particles in combination with controlled-release particles in a ratio sufficient useful for delivering the desired dosages of active agents.

For example, the immediate-release particles can comprise about 12.5 mg of promethazine, and the controlled-release particles can comprise about 7.5 mg of hydrocodone (or 7.5 mg of oxycodone) and about 325 mg of acetaminophen.

In another aspect of the present invention, the components are released from a multi-layered tablet that comprise at least a first layer, a second layer and a third layer. Wherein, the layers containing an agent (such as an opioid analgesic, a non-opioid analgesic and an antihistamine) can be optionally separated by one or more layers of inert materials. In one embodiment the layers containing an agent have similar rates of release, e.g. all are immediate release or all are controlled-release. In an alternative embodiment the layers have different rates of release. In this aspect at least one layer is an immediate release layer and at least one layer is a controlled release layer. For example in one embodiment the multilayer tablet comprises at least three layers, each of which contains a different agent, such as: layer one contains promethazine; layer two comprises hydrocodone or oxycodone; and layer three comprises acetaminophen. In this embodiment the promethazine layer may be designed for immediate-release, while the other two layers may be designed for controlled-release.

In another embodiment a composition comprising an opioid analgesic agent, a non-opioid analgesic agent and an antihistamine agent is administered to a subject. In this embodiment the antihistamine component can be formulated for immediate release or a controlled release which is faster than the release of the opioid analgesic agent and, optionally, the non-opioid analgesic agent. In one embodiment the composition comprises hydrocodone or oxycodone, acetaminophen and promethazine.

In another embodiment a composition comprising an opioid analgesic agent, a non-opioid analgesic agent and an antihistamine agent is administered to a subject; wherein the amounts and release rates of the opioid analgesic agent and the antihistamine agent are effective to reduce at least one side affect of opioid treatment in a subject. In one embodiment the composition comprises hydrocodone or oxycodone, acetaminophen and promethazine.

Additives

The present compositions can further comprise suitable additives, including, but not limited to, diluents, binders, surfactants, lubricants, glidants, coating materials, plasticizers, coloring agents, flavoring agents, or pharmaceutically inert materials.

Examples of diluents include, for example, cellulose; cellulose derivatives such as microcrystalline cellulose and the like; starch; starch derivatives such as corn starch, cyclodextrin and the like; sugar; sugar alcohol such as lactose, D-mannitol and the like; inorganic diluents such as dried aluminum hydroxide gel, precipitated calcium carbonate, magnesium aluminometasilicate, dibasic calcium phosphate and the like.

Examples of binders include, for example, hydroxypropylcellulose, methylcellulose, hydroxypropylmethylcellulose, povidone, dextrin, pullulane, hydroxypropyl starch, polyvinyl alcohol, scacia, agar, gelatin, tragacanth, macrogol and the like.

Examples of surfactants include, for example, sucrose esters of fatty acids, polyoxyl stearate, polyoxyethylene hydrogenated castor oil, polyoxyethylene polyoxypropylene glycol, sorbitan sesquioleate, sorbitan trioleate, sorbitan monostearate, sorbitan monopalmitate, sorbitan monolaurate, polysorbate, glyceryl monostearate, sodium lauryl sulfate, lauromacrogol and the like.

Examples of lubricants include, for example, stearic acid, calcium stearate, magnesium stearate, talc and the like.

Examples of glidants include, for example, dried aluminium hydroxide gel, magnesium silicate and the like.

Examples of coating materials include, for example, hydroxypropylmethyl cellulose 2910, aminoalkyl methacrylate copolymer E, polyvinylacetal diethylaminoacetate, macrogol 6000, titanium oxide and the like. Examples of plasticizers include, for example, triethyl citrate, triacetin, macrogol 6000 and the like.

EXAMPLES

Examples of Hydrocodone-Acetaminophen-Promethazine-Containing Analgesics

Example 1

Analgesic Composition A
Agents mg/Tablet

| Hydrocodone Bitartrate | 7.5 mg |
|---|---|
| Acetaminophen | 325 mg |
| Promethazine | 12.5 mg |

Example 2

The composition of Example 1 is orally administered with water to a subject having a tendency to exhibit adverse effects of gastric upset, nausea, vomiting, or skin rash. Such subjects, upon taking the composition set forth in Example 1 would receive a therapeutically effective amount of promethazine in their blood stream. The promethazine would reduce the adverse effects that such a target population would otherwise exhibit.

In another example, the dosage form is a bi-layered tablet, in which the first layer is an immediate-release layer comprising 12.5 mg of promethazine hydrochloride and the second layer is a controlled-release layer comprising 12.5 mg of promethazine hydrochloride, 15 mg of hydrocodone bitartrate, and 325 mg of acetaminophen.

Examples of Oxycodone Hydrochloride, Acetaminophen, Promethazine Containing Analgesics Example 3

Analgesic Composition B
Agents mg/Tablet

| Oxycodone HCl | 7.5 mg or 5 mg |
|---|---|
| Acetaminophen | 325 mg |
| Promethazine | 12.5 mg |

Example 4

The composition of Example 3 is orally administered with water to a subject having a tendency to exhibit adverse effects of gastric upset, nausea, vomiting, or skin rash. Such subjects, upon taking the composition set forth in Example 3 would receive a therapeutically effective amount of promethazine which will reduce the adverse effects that such a target population would otherwise exhibit.

In one embodiment, the dosage form is a bi-layered tablet, in which the first layer is an immediate-release layer comprising 12.5 mg of promethazine hydrochloride, and the second layer is a controlled-release layer comprising 12.5 mg of promethazine hydrochloride, 15 mg of oxycodone HCl, and 325 mg of acetaminophen.

What is claimed is:

1. A method for treating pain, and reducing or preventing nausea or vomiting associated with an opioid analgesic, the method comprising administering a solid oral pharmaceutical composition to a subject in need thereof, wherein the solid oral pharmaceutical composition comprises:
    a layer formulated for immediate-release comprising an antiemetic, wherein the antiemetic is promethazine or a pharmaceutically acceptable salt thereof that is present in an amount of about 12.5 mg or 25 mg; and
    a layer formulated for controlled-release comprising an opioid analgesic that is present in an amount of 1 mg to about 20 mg and a non-opioid analgesic that is present in an amount of about 200-600 mg,
wherein the solid oral pharmaceutical composition provides an effective amount of the antiemetic to reduce or prevent nausea associated with the opioid analgesic or vomiting associated with the opioid analgesic in the subject in need thereof, and an effective amount of the opioid analgesic and the non-opioid analgesic to treat pain in the subject in need thereof.

2. The method of claim 1, wherein the promethazine or the pharmaceutically acceptable salt thereof is present in an amount of about 12.5 mg.

3. The method of claim 1, wherein the promethazine or the pharmaceutically acceptable salt thereof is present in an amount of 25 mg.

4. The method of any one of claims 2 or 3, wherein the pharmaceutically acceptable salt of the promethazine is promethazine hydrochloride.

5. The method of claim 1, wherein the pharmaceutically acceptable salt of the promethazine is promethazine hydrochloride.

6. The method of claim 1, wherein the opioid analgesic is hydrocodone or a pharmaceutically acceptable salt thereof, or oxycodone or a pharmaceutically acceptable salt thereof.

7. The method of claim 6, wherein the opioid analgesic is hydrocodone bitartrate.

8. The method of claim 6, wherein the opioid analgesic is oxycodone hydrochloride.

9. The method of claim 1, wherein the non-opioid analgesic is acetaminophen or a pharmaceutically acceptable salt thereof.

10. The method of claim 1, wherein the solid oral pharmaceutical composition is a bi-layer tablet.

11. A method for treating pain, and reducing or preventing nausea or vomiting associated with an opioid analgesic, the method comprising administering a solid oral pharmaceutical composition to a subject in need thereof, wherein the solid oral pharmaceutical composition comprises:
    a layer formulated for immediate-release comprising a single antiemetic; and
    a layer formulated for controlled-release comprising a non-opioid analgesic and an opioid analgesic, wherein the opioid analgesic is hydrocodone or a pharmaceutically acceptable salt thereof, or oxycodone or a pharmaceutically acceptable salt thereof, and the opioid analgesic is present in an amount of about 1 mg to about 15 mg, and wherein the non-opioid analgesic is present in an amount of about 200-600 mg, wherein the solid oral pharmaceutical composition provides an effective amount of the antiemetic to reduce or prevent nausea associated with the opioid analgesic or vomiting associated with the opioid analgesic in the subject in need thereof, and an effective amount of the opioid analgesic and the non-opioid analgesic to treat pain in the subject in need thereof.

12. The method of claim 11, wherein the opioid analgesic is hydrocodone or the pharmaceutically acceptable salt thereof, and is present in an amount of about 7.5 mg.

13. The method of claim 11, wherein the opioid analgesic is hydrocodone or the pharmaceutically acceptable salt thereof, and is present in an amount of 5 mg.

14. The method of claim 12, wherein the opioid analgesic is hydrocodone bitartrate.

15. The method of claim 11, wherein the opioid analgesic is oxycodone or the pharmaceutically acceptable salt thereof, and is present in an amount of about 7.5 mg.

16. The method of claim 11, wherein the opioid analgesic is hydrocodone bitartrate.

17. The method of claim 11, wherein the opioid analgesic is oxycodone hydrochloride.

18. The method of claim 11, wherein the antiemetic is promethazine or a pharmaceutically acceptable salt thereof.

19. The method of claim 18, wherein the antiemetic is promethazine hydrochloride.

20. The method of claim 11, wherein the non-opioid analgesic is acetaminophen or a pharmaceutically acceptable salt thereof.

21. The method of claim 11, wherein the solid oral pharmaceutical composition is a bi-layer tablet.

22. A method for treating pain, and reducing or preventing nausea or vomiting associated with an opioid analgesic, the method comprising administering a solid oral pharmaceutical composition to a subject in need thereof, wherein the solid oral pharmaceutical composition comprises:
   a layer formulated for immediate-release comprising an antiemetic that is present in an amount of about 12.5 mg or 25 mg; and
   a layer formulated for controlled-release comprising an opioid analgesic and a non-opioid analgesic, wherein the opioid analgesic is present in an amount of 1 mg to about 20 mg, and wherein the non-opioid analgesic is acetaminophen or a pharmaceutically acceptable salt thereof that is present in about 200-600 mg, wherein the solid oral pharmaceutical composition provides an effective amount of the antiemetic to reduce or prevent nausea associated with the opioid analgesic or vomiting associated with the opioid analgesic in the subject in need thereof, and an effective amount of the opioid analgesic and the non-opioid analgesic to treat pain in the subject in need thereof.

23. The method of claim 22, wherein the acetaminophen or the pharmaceutically acceptable salt thereof is present in an amount of about 325 mg.

24. The method of claim 22, wherein the opioid analgesic is hydrocodone or a pharmaceutically acceptable salt thereof, or oxycodone or a pharmaceutically acceptable salt thereof.

25. The method of claim 24, wherein the opioid analgesic is hydrocodone bitartrate.

26. The method of claim 24, wherein the opioid analgesic is oxycodone hydrochloride.

27. The method of claim 22, wherein the antiemetic is promethazine or a pharmaceutically acceptable salt thereof.

28. The method of claim 27, wherein the antiemetic is promethazine hydrochloride.

29. The method of claim 22, wherein the solid oral pharmaceutical composition is a bi-layer tablet.

30. The method of claim 15, wherein the pharmaceutically acceptable salt of the oxycodone is oxycodone hydrochloride.

31. The method of claim 11, wherein the oxycodone or the pharmaceutically acceptable salt thereof is present in an amount of 5 mg.

32. The method of claim 31, wherein the pharmaceutically acceptable salt of the oxycodone is oxycodone hydrochloride.

33. The method of claim 1, wherein the solid oral pharmaceutical composition further comprises an opioid antagonist or an additional agent for reducing abuse and/or diversion.

34. The method of claim 11, wherein the solid oral pharmaceutical composition further comprises an opioid antagonist or an additional agent for reducing abuse and/or diversion.

35. The method of claim 22, wherein the solid oral pharmaceutical composition further comprises an opioid antagonist or an additional agent for reducing abuse and/or diversion.

* * * * *